(12) United States Patent
Nielsen et al.

(10) Patent No.: US 9,670,494 B2
(45) Date of Patent: Jun. 6, 2017

(54) GENETICALLY ENGINEERED YEAST CELLS

(71) Applicants: Jens Nielsen, Gothenburg (SE); Verena Siewers, Göteborg (SE); Yun Chen, Göteborg (SE); Laurent Daviet, Geneva (CH); Michel Schalk, Geneva (CH)

(72) Inventors: Jens Nielsen, Gothenburg (SE); Verena Siewers, Göteborg (SE); Yun Chen, Göteborg (SE); Laurent Daviet, Geneva (CH); Michel Schalk, Geneva (CH)

(73) Assignee: FIRMENICH SA, Geneva (CH)

( * ) Notice: Subject to any disclaimer, the term of this patent is extended or adjusted under 35 U.S.C. 154(b) by 434 days.

(21) Appl. No.: 14/370,959

(22) PCT Filed: Dec. 17, 2012

(86) PCT No.: PCT/EP2012/075814
§ 371 (c)(1),
(2) Date: Jul. 7, 2014

(87) PCT Pub. No.: WO2013/102554
PCT Pub. Date: Jul. 11, 2013

(65) Prior Publication Data
US 2015/0079646 A1 Mar. 19, 2015

(30) Foreign Application Priority Data
Jan. 6, 2012 (EP) .................................... 12150341

(51) Int. Cl.
*C12P 7/16* (2006.01)
*C12N 9/90* (2006.01)
*C12N 15/81* (2006.01)
*C12N 9/04* (2006.01)
*C12N 9/10* (2006.01)
*C12N 9/00* (2006.01)
*C12P 5/00* (2006.01)
*C12P 7/62* (2006.01)
*C12N 9/02* (2006.01)

(52) U.S. Cl.
CPC ........... *C12N 15/81* (2013.01); *C12N 9/0006* (2013.01); *C12N 9/0008* (2013.01); *C12N 9/1025* (2013.01); *C12N 9/1029* (2013.01); *C12N 9/93* (2013.01); *C12P 5/007* (2013.01); *C12P 7/16* (2013.01); *C12P 7/625* (2013.01); *C12Y 101/01002* (2013.01); *C12Y 102/01004* (2013.01); *C12Y 203/01009* (2013.01); *C12Y 602/01001* (2013.01); *Y02E 50/10* (2013.01)

(58) Field of Classification Search
CPC .................................... C12P 7/16; C12N 9/93
See application file for complete search history.

(56) References Cited

U.S. PATENT DOCUMENTS

2009/0053797 A1* 2/2009 Shiba .................... C12P 23/00 435/254.21
2013/0034884 A1* 2/2013 Burgard ................. C12N 15/52 435/126

FOREIGN PATENT DOCUMENTS

| WO | WO2007024718 A2 | 3/2007 |
| WO | WO2008080124 | 7/2008 |
| WO | WO2009109597 | 9/2009 |
| WO | WO2011090753 | 7/2011 |

OTHER PUBLICATIONS

Verduyn et al., Yeast 1992, vol. 8, pp. 501-517.
Madison et al., Microbiol and Mol Biol Rev, 1999, vol. 63 No. 1, p. 21.
Partow et al., Yeast 2010, vol. 27, pp. 955-964.
Peoples et al., J. Biol Chem 1989, vol. 264, pp. 15293-15297.
Peoples et al., J. Biol. Chem 1989 vol. 264, pp. 15298-15303.
Ro et al., Nature 2006, vol. 440, pp. 940-943.
Shiba et al., Metabolic Engineering, 2007, vol. 9, No. 2, pp. 160-168.
Siewers et al., Metabolic Engineering, vol. 11, 2009, pp. 391-397.
Starai et al., J Biol Chem, 2005, vol. 280, pp. 26200-26205.
Sybirna et al., Yeast 2010, vol. 27, p. 954.
Tyo Keith E. et al., Appl and Environ. Microbiol, 2006 vol. 72 No. 5, pp. 3412-3417.
International Search Report and Written Opinion, application PCT/EP2012/075814, mailed Feb. 26, 2013.
Becker et al., Microbial Cell Factories, 2008, 7-8.
Brooks B Bond-Watts et al., Nat Chem Biol, 2011, vol. 7, p. 222.
Carlson et al., J Biotechnol, vol. 124, 2006, p. 561.
Erdeniz et al., Genome Res. , vol. 7, 1997, pp. 1174-1183.
Gardner et al., J Biol Chem, 1999, vol. 274 p. 31671.
Gietz et al., Nucleic Acids Res.1992 , vol. 20 No. 6, p. 1425.
Guldener et al., Nucleic Acids Res. 1996, vol. 24 No. 13, pp. 2519-2524.
Hamilton et al., Nucleic Acids Res. 1987, vol. 15, No. 8, pp. 3581-93.
Karr et al., Appl and Environ. Microbiol 1983, vol. 46 No. 6, pp. 1339-1344.
Bussey,H., et al., *Saccharomyces cerevisiae* S288c acetyl-CoA C-acetyltransferase (ERG10), mRNA., NCBI GenBank Accession No: NM_001183842, Oct. 28, 2016.
Rocci, L. and Schalk, M., Clausena lansium Tps2-1 mRNA, complete cds., NCBI GenBank Accession No: HQ452480, Dec. 11, 2010.
Steen, E. J., et al., Metabolic engineering of *Saccharomyces cerevisiae* for the production of n-butanol, Microbial Cell Factories, 2008, 7:36, 8 pp.

* cited by examiner

*Primary Examiner* — Maryam Monshipouri

(57) ABSTRACT

The present invention relates to yeast cells producing high levels of acetoacetyl-CoA. It also relates to a method for making such yeast cells and to the use of such yeast cells in a method for producing acetyl-CoA derived products.

11 Claims, 7 Drawing Sheets

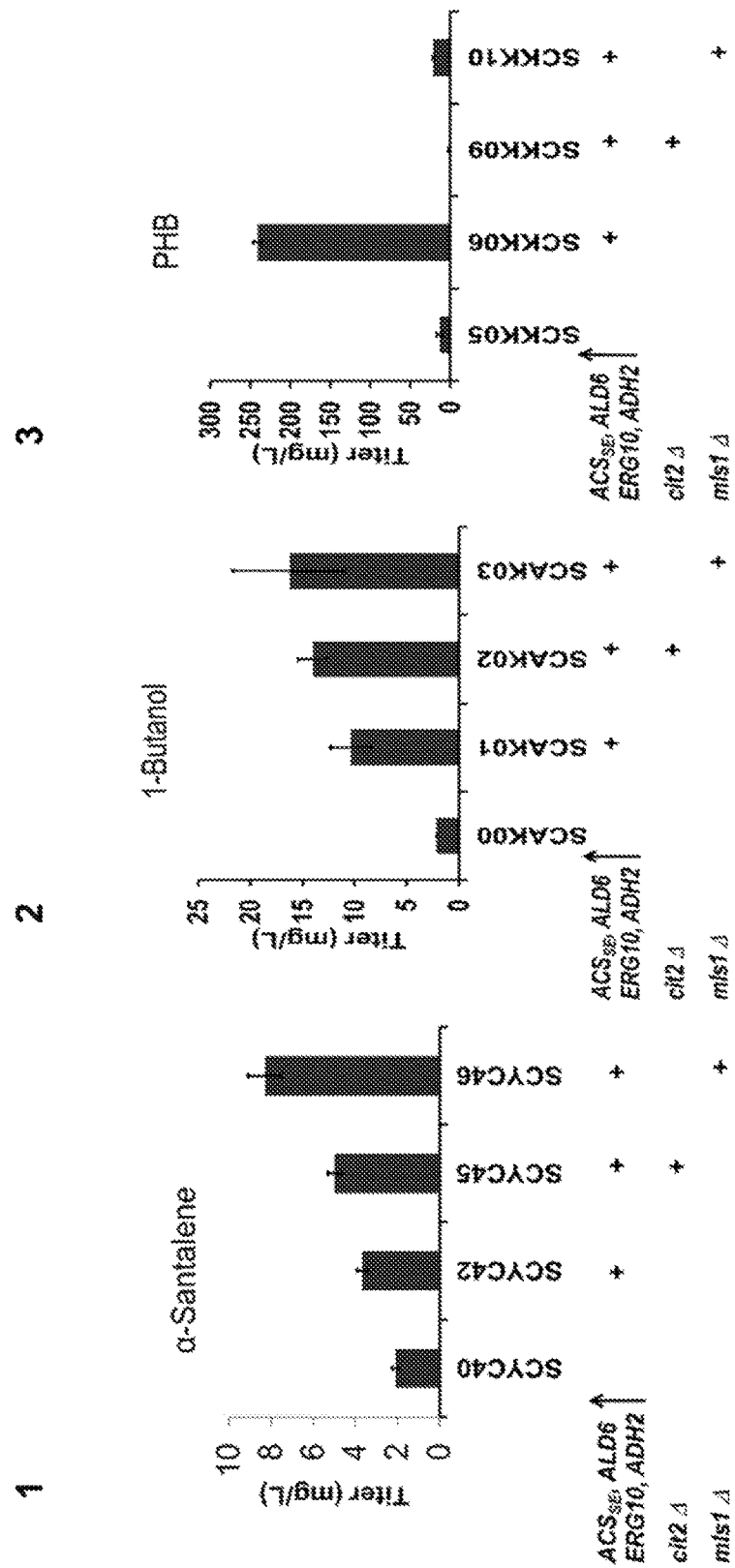

US 9,670,494 B2

GENETICALLY ENGINEERED YEAST CELLS

RELATED APPLICATIONS

This application is a national stage application (under 35 U.S.C. §371) of PCT/EP2012/075814, filed Dec. 17, 2012, which claims benefit of European application 12150341.1, filed Jan. 6, 2012.

TECHNICAL FIELD

The present invention relates to yeast cells producing high levels of acetyl-CoA and acetoacetyl-CoA. It also relates to a method for making such yeast cells and to the use of such yeast cells in a method for the production of acetyl-CoA derived products.

BACKGROUND OF THE INVENTION

The biosynthesis of a wide range of industrially interesting natural products in engineered host cells (so called cell factories) could tap the unrealized commercial potential of these natural resources. Thus, there is growing interest in developing platform cell factories that can efficiently convert cheap sources of carbon into so-called precursor metabolites that are then further converted into the product of interest. One of these key metabolites is acetyl-CoA that is used as precursor for the production of a wide range of industrially interesting products including isoprenoids (mainly used as flavours and fragrances, biodiesels, antimalarial and anticancer drugs, antibiotics, rubber, dietary supplements, food ingredients and vitamins), polyketides (antibiotics, anticancer drugs and immunosuppressors), lipids (such as dietary supplements, pharmaceuticals and biodiesels), polyhydroxyalkanoates and 1-butanol (FIG. 1).

In a former study, engineering of the pyruvate dehydrogenase bypass in *Saccharomyces cerevisiae* was shown to enhance the supply of acetyl-CoA and to increase the production of the sesquiterpene compound amorphadiene (*Metab Eng* 2007, 9:160; WO 2007024718). This was achieved by over-production of an acetaldehyde dehydrogenase and introduction of an heterologous *Salmonella enterica* acetyl-CoA synthetase variant into the host cell.

However, there remains a need to further increase the acetyl-CoA production, which when met should increase production of any desired acetyl-CoA derived product. The present invention addresses this issue using a combined push-pull-block strategy, thus providing a platform cell factory that can be used to improve the production of acetyl-CoA derived products. This is exemplified using three different compounds derived from acetyl-CoA.

SUMMARY OF THE INVENTION

In a first aspect the invention provides a yeast cell modified by overexpression of an aldehyde dehydrogenase and an acetyl-CoA synthetase (ACS), characterized in that an alcohol dehydrogenase and an acetoacetyl-CoA synthase are further overexpressed.

In another aspect it provides a method of making a modified yeast cell comprising over-expressing an aldehyde dehydrogenase and an acetyl-CoA synthetase (ACS), characterized in that said method further comprises over-expressing an alcohol dehydrogenase and an acetoacetyl-CoA synthase.

In a further aspect, it provides a method for producing increased levels of a product derived from acetyl-CoA comprising culturing the yeast cell of the invention, which is capable of producing such product, under conditions conducive to the production of said product.

BRIEF DESCRIPTION OF THE DRAWINGS

FIG. 5A-B: Engineering of yeast acetyl-CoA metabolism improves the production of α-santalene (A1 and B1), 1-butanol (A2 and B2) and polyhydroxybutyrate (PHB) (A3 and B3). Schematic representations of the reconstituted biosynthetic pathways are shown in the upper panels (A). The following enzymes are derived from other organisms: Sts, *Clausena lansium*; PhaA, PhaB, PhaC, *Ralstonia eutropha*; Hbd, Crt, AdhE2, *Clostridium beijerinckii*; Ter, *Treponema denticola*. A truncated version of the endogenous HMG1 (tHMG1) is overexpressed for α-santalene production. All engineered *S. cerevisiae* strains are described in the text. Cultures were grown in 100 ml-shake flasks containing 20 ml defined minimal medium with 20 g/L glucose as the carbon source. α-santalene levels were quantified by GC-MS, 1-butanol and PHB levels were quantified by HPLC. tHMG1, hydroxymethylglutaryl-CoA reductase; Sts, α-santalene synthase; PhaA, acetyl-CoA acetyltransferase; PhaB, acetoacetyl-CoA reductase; PhaC, poly (3-hydroxybutyrate) polymerase; Hbd, 3-hydroxybutyryl-CoA dehydrogenase; Crt, crotonase; Ter, trans enoyl-coA reductase; AdhE2, butyraldehyde dehydrogenase/butanol dehydrogenase.

DETAILED DESCRIPTION OF THE INVENTION

Figure 1:
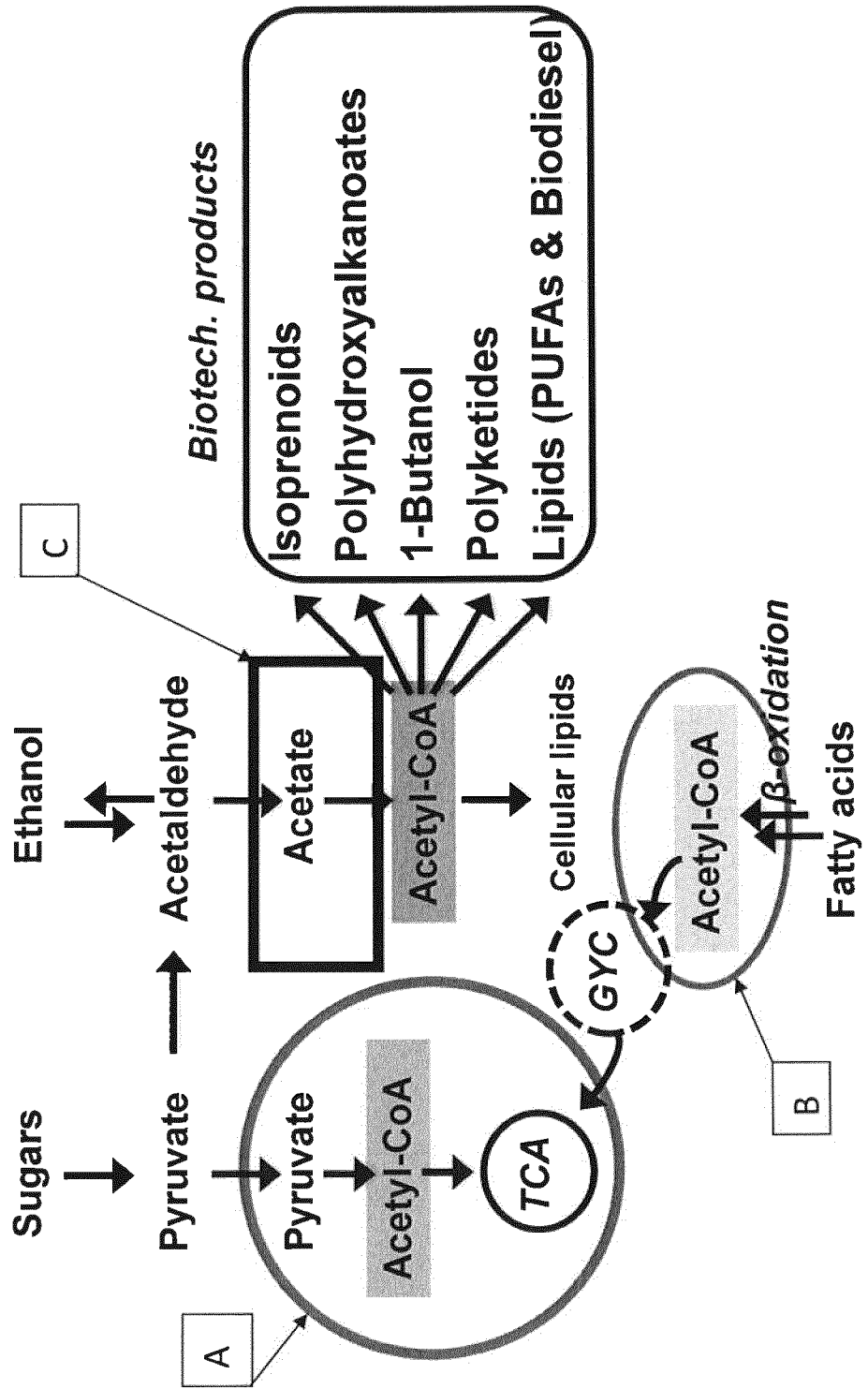
FIG. 1: Simplified overview of acetyl-CoA metabolism in *Saccharomyces cerevisiae*. Acetyl-CoA is a key primary metabolite localized in three different subcellular compartments: the cytosol (C), the mitochondria (A), and the peroxisome (B). There is no direct transport of acetyl-CoA between the three compartments, and the biosynthesis of acetyl-CoA in the three compartments involves different metabolic pathways. In the mitochondria, acetyl-CoA is formed from pyruvate by the pyruvate dehydrogenase complex. In the cytosol, acetyl-CoA is formed from acetate by acetyl-CoA synthase. In the peroxisome, acetyl-CoA can be formed from both acetate (also by acetyl-CoA synthase, not shown) and from fatty acids by β-oxidation. In the mitochondria, the primary fate of acetyl-CoA is oxidation via the tricarboxylic acid (TCA) cycle. Acetyl-CoA in the peroxisome can, via the glyoxylate cycle (GYC), be converted to $C_4$ organic acids (malate and succinic acid) that can be transferred to the mitochondria for oxidation via malic enzyme and the TCA cycle. The primary fate of acetyl-CoA in the cytosol is to serve as precursor for cellular lipids (fatty acids and ergosterol). Many industrially interesting biotechnological products are derived from acetyl-CoA and the biosynthesis of most of these occurs in the cytosol. A platform yeast cell factory for all these products should therefore have redirection of carbon towards the acetyl-CoA in the cytosol.

The yeast cell of the present invention has the surprising advantage of producing increased levels of acetyl-CoA and acetoacetyl-CoA, thus enabling production of increased levels of useful products derived therefrom, such as for example terpenoids, 1-butanol and polyhydroxy butyrate.

The yeast cell can be any type of yeast cells. Preferably, the yeast cell is capable of producing ethanol. More preferably it is selected from yeast of the *Saccharomyces, Zygosaccharomyces, Kluyveromyces, Candida, Hansenula, Debaryomyces, Mucor, Pichia* and *Torulopsis* genera. Most preferably, it is *Saccharomyces cerevisiae*.

The strategy involves a push of carbon from ethanol via acetaldehyde to cytosolic acetyl-CoA. This is achieved by overexpressing an alcohol dehydrogenase such as the endogenous ADH2 gene in *Saccharomyces cerevisiae* and an aldehyde dehydrogenase such as the NADP-dependent ALD6 gene in *Saccharomyces cerevisiae* and an acetyl-CoA synthase such as a the ACS variant (L641P) from *Salmonella enterica* ($ACS_{SE}$). $ACS_{SE}$ contains a point mutation that prevents the enzyme from being inhibited by acetylation (*J Biol Chem* 2005, 280:26200), and the use of this variant particularly efficiently redirects flux from acetaldehyde to acetyl-CoA in the cytosol.

To ensure pulling of acetyl-CoA towards the three products of interest, an acetyl-CoA C-acetyltransferase that catalyzes the conversion of acetyl-CoA to acetoacetyl-CoA (AcAcCoA) is also over-expressed. AcAcCoA is a common precursor for the three products used to evaluate the acetyl-CoA platform strain. In *S. cerevisiae*, the ERG10 gene encodes an acetyl-CoA C-acetyltransferase.

In a preferred embodiment of the invention, the yeast cell is further modified by deletion of a gene encoding a cytosolic malate synthase or a gene encoding a peroxisomal citrate synthase from the yeast cell genome. Such deletion have the advantage of avoiding consumption of acetyl-CoA in the glyoxylate cycle, so as to increase the availability of acetyl-CoA for other pathways, such as those leading to terpenoids, 1-butanol or polyhydroxy butyrate.

To further reduce carbon loss from the precursor acetyl-CoA pool, reactions that involve consumption of acetyl-CoA are thus preferably removed. This involves removing two key reactions of the glyoxylate cycle (GYC), namely a peroxisomal citrate synthase and a cytosolic malate synthase encoded by CIT2 and by MLS1 in *S. cerevisiae*, respectively.

The yeast cell of the invention can be made by a method comprising over-expressing an aldehyde dehydrogenase, an acetyl-CoA synthetase (ACS), an alcohol dehydrogenase and an acetoacetyl-CoA synthase.

In a preferred embodiment of the invention, the method further comprises deleting a gene encoding a cytosolic malate synthase or a gene encoding a peroxisomal citrate synthase from the yeast cell genome.

The aldehyde dehydrogenase, the ACS, the alcohol dehydrogenase, the acetoacetyl-CoA synthase, the cytosolic malate synthase, the peroxisomal citrate synthase and the yeast cell are as defined above in any embodiment of the invention relating to the yeast cell.

Overexpression of the aldehyde dehydrogenase, the ACS, the alcohol dehydrogenase, the acetoacetyl-CoA synthase can be performed using episomal yeast expression vectors or through genomic integration using methods well-known in the art. These methods are standard but can be for example carried out as described in *Methods in Yeast Genetics*, 2005 Ed., Cold Spring Harbor Laboratory press.

Malate synthase and citrate synthase gene deletions can be performed using any method well-known to the person skilled in the art for gene deletion, such as for example a cloning-free, PCR-based allele replacement method such as described in *Genome Res.* 1997, 7:1174 or any other gene deletion methods.

By culturing the yeast cells of the invention under suitable conditions, secondary metabolites can be produced. Preferably, said metabolites are produced at increased level, i.e. more secondary metabolite is produced when the yeast cell of the invention is cultured than when the un-transformed yeast cell is cultured.

The yeast cell must be capable of producing the desired secondary metabolite. This means that either the yeast cell is naturally capable of producing such secondary metabolite or, alternatively, the yeast cell is transformed with additional genes that are necessary for the production of such metabolite. Further modification of the yeast cell as described above has the effect of increasing the level of secondary metabolite produced by the yeast cell not so modified.

For example, when the secondary metabolite is a terpenoid, the yeast cell can be transformed to express or over-express a terpene synthase capable of catalysing the conversion of an acyclic terpene precursor to such terpenoid. This applies for all acyclic terpene precursors such as for example geranylpyrophosphate, farnesylpyrophosphate and geranylgeranylpyrophosphate, depending of the terpenoid that is intended to be produced. Terpenoids are natural products known for their flavor and fragrance, cosmetic, pharmaceutical and antimicrobial properties. These compounds are made up of five carbon units called isoprene units and are classified by the number of these units present in their structure. Thus monoterpenes, sesquiterpenes and diterpenes are terpenes containing 10, 15 and 20 carbon atoms, respectively. Sesquiterpenes, for example, are widely found in the plant kingdom. Many monoterpene, sesquiterpene and diterpene molecules are known for their flavor and fragrance properties and their cosmetic, medicinal and antimicrobial effects. Over 300 sesquiterpene hydrocarbons and 3,000 sesquiterpenoids have been identified and many new structures are identified each year. Plant extracts obtained by different means such as steam distillation or solvent extraction are used as source of terpenes. Terpene molecules are often used as such, but in some cases chemical reactions are used to transform the terpenes into other high value molecules. The majority of the terpenes in use today are natural products extracted from diverse organisms (plant, marine organisms, . . . ). However, most of these source organisms are not amenable to large-scale cultivation necessary to produce commercially viable quantities nor to genetic manipulation to increase their production capabilities. Furthermore, many of these natural products have complex structures and are currently not accessible by chemical means.

Examples of preferred sesquiterpenes include α-santalene, patchoulol, β-santalene, valencene, cubebol, zizaene, amorpha 4,11-diene, humulene, aristolochene, bergamotene, zingiberene, farnesene, caryophyllene, isodaucene, sesquithujene, avermitilol, eudesmol, vetispiradiene, longifolene, cyclocopacamphene, isolongifolene, germacrene, bicyclogermacrene, bisabolol, germacradienol, hedycaryol, barbatene, epi-cedrol, epi-aristolochene, sesquisabinene, cuprene, selinene, copaene, macrocarpene, cadinol, intermedeol, nerolidol, sesquisabinene, muurola-3,5-diene, curcumene and epi-beta santalene. More preferred sesquiterpenes include α-santalene, patchoulol, β-santalene, valencene, cubebol, zizaene, amorpha 4,11-diene. Even more preferably, the sesquiterpene is patchoulol or α-santalene.

Examples of preferred diterpenes include sclareol, labdendiol and taxadiene. Examples of preferred monoterpenes include limonene, pinene, myrcene, camphene, phellandrene, terpinolene, ocimene, linalool, cineole, geraniol, terpinene, fenchol, carene, sabinene.

Another example of a metabolite that can be made using the method of the invention is 1-butanol. 1-Butanol is considered as a possible gasoline replacement, because it has higher energy density while it is less corrosive and less water soluble than ethanol.

A further example of a metabolite that can be made using the method of the invention is polyhydroxy butyrate (PHB). PHB is a member of a family of commercially interesting biodegradable biopolymers.

The yeast cells of the invention can be cultured in any type of growth medium adapted to such yeast species. Such media are well-known in the art and do not warrant a more complete description here, which would in any case not be exhaustive. The growth medium is preferably also adapted to the types of promoters used to over-express the above-mentioned genes. For example, if the over-expressed genes are under the control of glucose-regulated promoter the growth medium preferably comprises glucose.

EXAMPLES

The invention is now described in further details by the way of the following examples.

Example 1

Yeast Strains and Media

*Saccharomyces cerevisiae* strain CEN.PK113-11C (MATa SUC2 MAL2-8$^c$ ura3-52 his3-Δ1, kindly provided by P. Kötter, University of Frankfurt, Germany) was used as background strain. All yeast strains used in this study are summarized in Table 1.

TABLE 1

Yeast strains used in this study and relevant genotypes

| Strain name | Genotypes |
|---|---|
| CEN.PK113-11C | MATa SUC2 MAL2-8$^c$ ura3-52 his3-Δ1 |
| SCIYC32 | MATa SUC2 MAL2-8$^c$ ura3-52 his3-Δ1 cit2Δ |
| SCIYC33 | MATa SUC2 MAL2-8$^c$ ura3-52 his3-Δ1 mls1Δ |
| SCIYC40 | CEN.PK113-11C pICK01 pIYC04 |
| SCIYC42 | CEN.PK113-11C pICK01 pIYC08 |
| SCIYC45 | SCIYC32 pICK01 pIYC08 |
| SCIYC46 | SCIYC33 pICK01 pIYC08 |
| SCKK05 | CEN.PK113-11C pPHB-pha pIYC04 |
| SCKK06 | CEN.PK113-11C pPHB-pha pIYC08 |
| SCKK09 | SCIYC32 pPHB-pha pIYC08 |
| SCKK10 | SCIYC33 pPHB-pha pIYC08 |
| SCAK00 | CEN.PK113-11C pAK1 pIYC04 |
| SCAK01 | CEN.PK113-11C pAK1 pIYC08 |
| SCAK02 | SCIYC33 pAK1 pIYC08 |
| SCAK03 | SCIYC32 pAK1 pIYC08 |

Engineered yeast strains were selected on synthetic dextrose (SD) (*Metabolic Engineering* 2009, 11:391) medium without uracil and/or histidine where appropriate. *S. cerevisiae* strains were grown in defined minimal medium (*Yeast* 1992, 8:501) with 20 g/L glucose. For the production of α-santalene, a 10% (v/v) dodecane overlay was added to the culture at an OD$_{600}$ of 1 to capture α-santalene in the organic phase.

Example 2

ALD6, ACS$_{SE}$, ADH2 and ERG10 Yeast Expression Plasmids

To provide gene expression in a glucose-based cultivation, all yeast expression plasmids are based on two vectors pSP-G1 and pSP-G2 bearing constitutive promoters P$_{TEF1}$ and P$_{PGK1}$ (*Yeast* 2010, 27:955) (see Table 2 for the list of plasmids used in this study).

TABLE 2

Description of the plasmids used in this study

| Name | Gene expressed | Marker |
|---|---|---|
| pIYC04 | none | HIS3 |
| pIYC05 | P$_{TEF1}$-ACS$_{SE}$ P$_{PGK1}$-ALD6 | HIS3 |
| pIYC08 | P$_{TEF1}$-ACS$_{SE}$ P$_{PGK1}$-ALD6 P$_{TEF1}$-ERG10 P$_{HXT7}$-ADH2 | HIS3 |
| pICK01 | P$_{TEF1}$-Sts P$_{PGK1}$-tHMG1 | URA3 |
| pPHB-pha | P$_{TEF1}$-phaC P$_{PGK1}$-phaA P$_{TEF1}$-phaB | URA3 |
| pAK01 | P$_{TEF1}$-adhE2 P$_{PGK1}$-ter P$_{TEF1}$-crt P$_{PGK1}$-hbd | URA3 |

In order to provide additional restriction enzyme recognition sites downstream of each terminator (T$_{ADH1}$ and T$_{CYC1}$, respectively) the entire expression cassette was amplified by PCR using primers 17 and 18 (see Table 3 for the list of primers used in this study), cut with PvuII and ligated back into the vector backbone to generate pSP-GM1 and pSP-GM2, respectively. The 2.1-kb PvuII fragment from pSP-GM1, containing the P$_{TEF1}$-P$_{PGK1}$ bidirectional promoter cassette, was subsequently cloned into the PvuII sites of pESC-HIS (Stratagene) yielding pIYC04.

TABLE 3

Primers used for plasmids construction
(SEQ ID NO: 1 to 20)

| Primer number | Sequence (5' to 3') |
|---|---|
| 1 | CGCCGGATCCAAAACAATGACTAAGCTACACTTTGAC |
| 2 | CGCGCTCGAGTTACAACTTAATTCTGACAGC |
| 3 | TATTAGGCCGGCCCCGTGGAAATGAGGGGTATGC |
| 4 | GGCCGGCGGATCCTTTTTGATTAAAATTAAAAAAACT |
| 5 | GCGCGGATCCAAAACAATGTCTATTCCAGAAACTCAA |
| 6 | GCGATCCGGAACGTCAAGACGAAAAGTGAA |
| 7 | GCCGCGACTAGTAAAACAATGTCTCAGAACGTTT ACA |
| 8 | GCGGCCCGAGCTCTCATATCTTTTCAATGACAAT |
| 9 | CTATCTTCCGGAGCACACACCATAGCTTC |
| 10 | TCTAAACGCCGGCGAATTGGAGCGACCTCATGC |
| 11 | AAACTCCTAGGCCGTGGAAATGAGGGGTA |
| 12 | GTCAAAGGCGCGCCACGTCAAGACGAAAAGT |
| 13 | TACAATTGCTATTATTATCCTGCTCAGTGGTACTT |
| 14 | TCCAATTGTCAGTGAGCGAGGAAGCGGAAGAG |
| 15 | GAAGAACGCCGGCGGAGCGACCTCATGCTATACCTG |
| 16 | GTTGTTTCCGGATGTTACATGCGTACACGCGTC |
| 17 | GAACAACAGCTGGATAAAGGCGCGCCAAACGACCTAGGAATT GGAGCGACCTCATGCTATAC |
| 18 | GAACAACAGCTGGATAAACGCCGGCGAAACGATCCGGAGGAT CTTCGAGCGTCCCAAAAC |
| 19 | GTTGTTGCGG CCGCAAAACA ATGTCAACTC AACAAGTTTC ATCAG |
| 20 | GTTGTTTTAA TTAACTAATC GTCAAGCTTA ACGGG |

Restriction sites are underlined

Figure 3:
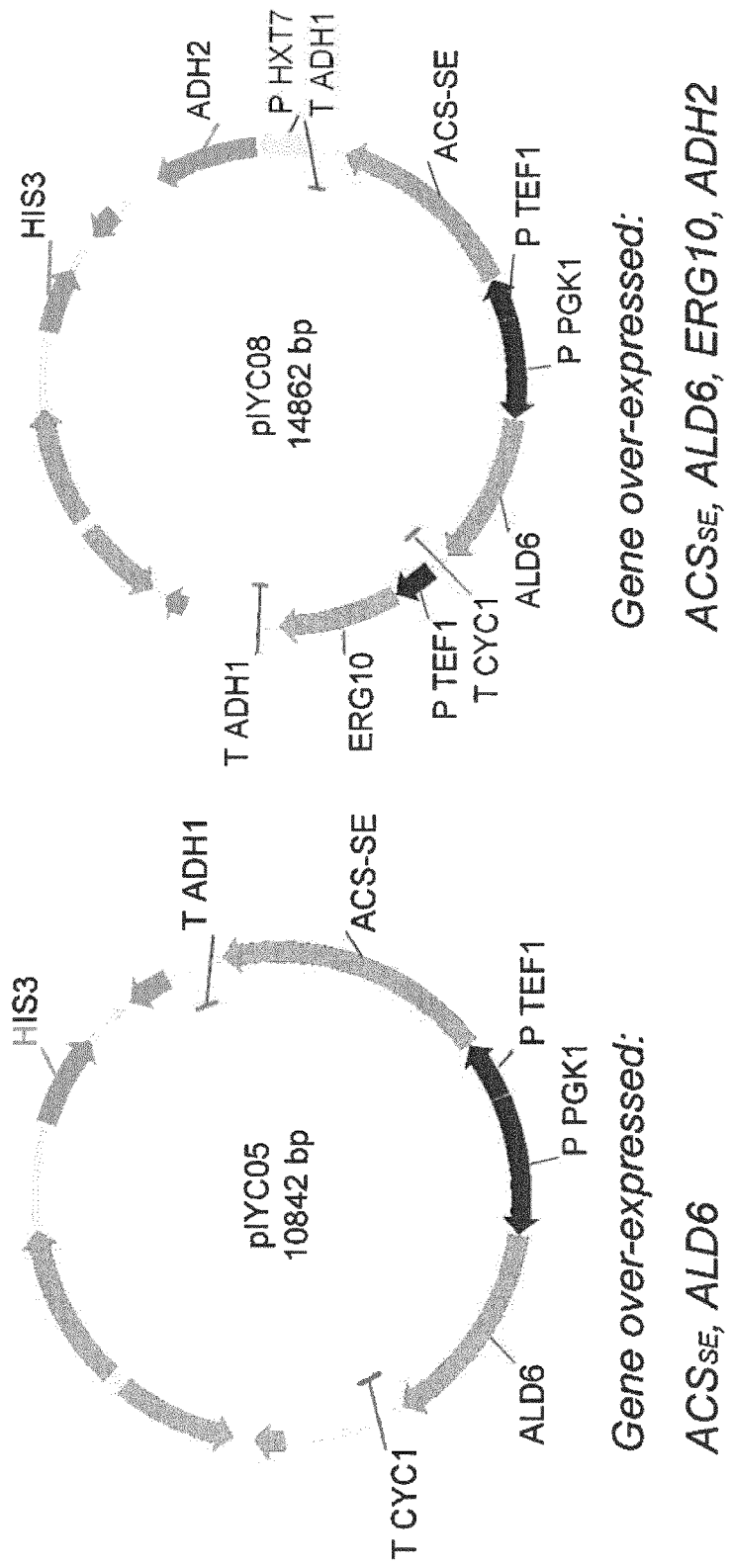
FIG. 3: Map of plasmids pIYC05 and pIYC08.

ALD6 (SEQ ID NO: 42) was PCR amplified from chromosomal DNA preparations of S. cerevisiae CEN.PK113-5D (MATa SUC2 MAL2-8$^c$ ura3-52) using the primer pair 1 and 2. Using these primers, the nucleotide sequence 5'-AAAACA-3' (Kozak sequence) was introduced immediately upstream of the start codon of ALD6 to improve translation efficiency (Nucleic Acids Res. 1987, 15:3581). This strategy was applied to all the other genes used in this study. The Salmonella enterica acetyl-CoA synthetase (ACS$_{SE}$) gene with a L641P mutation (J. Biol. Chem. 2005, 280:26200), ACS$_{SE}$ was codon optimized (SEQ ID NO: 52) and synthesized by DNA 2.0 (Menlo Park, Calif., USA) for high-level expression in yeast. A 1.5-kb BamHI/XhoI fragment containing a Kozak sequence and coding sequence of ALD6, and a 2.0-kb NotI/PacI fragment containing a Kozak sequence and ACS$_{SE}$ coding sequence were sequentially inserted into the corresponding sites of pIYC04, resulting in plasmid pIYC05 (FIG. 3).

To express the ADH2 gene under the control of glucose-based HXT7 promoter, a 0.6-kb promoter region of HXT7 was PCR amplified from CEN.PK113-5D using the primer pair 3 and 4. The amplified product was cleaved with BamHI/FseI and introduced into the BamHI and FseI sites of pSP-GM1 to replace the PGK1 promoter, yielding the plasmid pIYC06. A 1.5-kb fragment that contains the 1,047-bp complete sequence of ADH2 (SEQ ID NO: 41) and the 434-bp downstream sequence including its native terminator was amplified by PCR from CEN.PK113-5D using primers 5 and 6. Likewise, a 1.2-kb region of ERG10 (SEQ ID NO: 43) from CEN.PK113-5D was PCR amplified using primers 7 and 8. The 1.5-kb BamHI/XhoI fragment containing a Kozak sequence and ADH2, and the 1.2-kb SpeI/SacI fragment containing a Kozak sequence and ERG10 were sequentially inserted into the corresponding sites of pIYC06, resulting in plasmid pIYC07.

To overexpress ALD6, ACS$_{SE}$, ADH2 and ERG10 from a single plasmid, pIYC08 was then constructed. A 2.0-kb fragment containing the TEF1 promoter, ERG10, and the ADH1 terminator from pIYC07 was PCR amplified using primers 9 and 10 to introduce MreI/Kpn2I sites. The resulting DNA was cleaved with MreI/Kpn2I and inserted into the MreI/Kpn2I sites of pIYC05 to obtain plasmid pIYC05-1. Similarly, a cassette containing the HXT7 promoter, ADH2 and its native terminator from pIYC07 was PCR amplified using primers 11 and 12 to introduce two AscI sites. The amplified product was digested with AscI and subsequently cloned into the AscI sites of pIYC05-1, yielding plasmid pIYC08 (FIG. 3).

Example 3

Construction of an α-Santalene and tHMG1 Yeast Expression Vector

Figure 4:
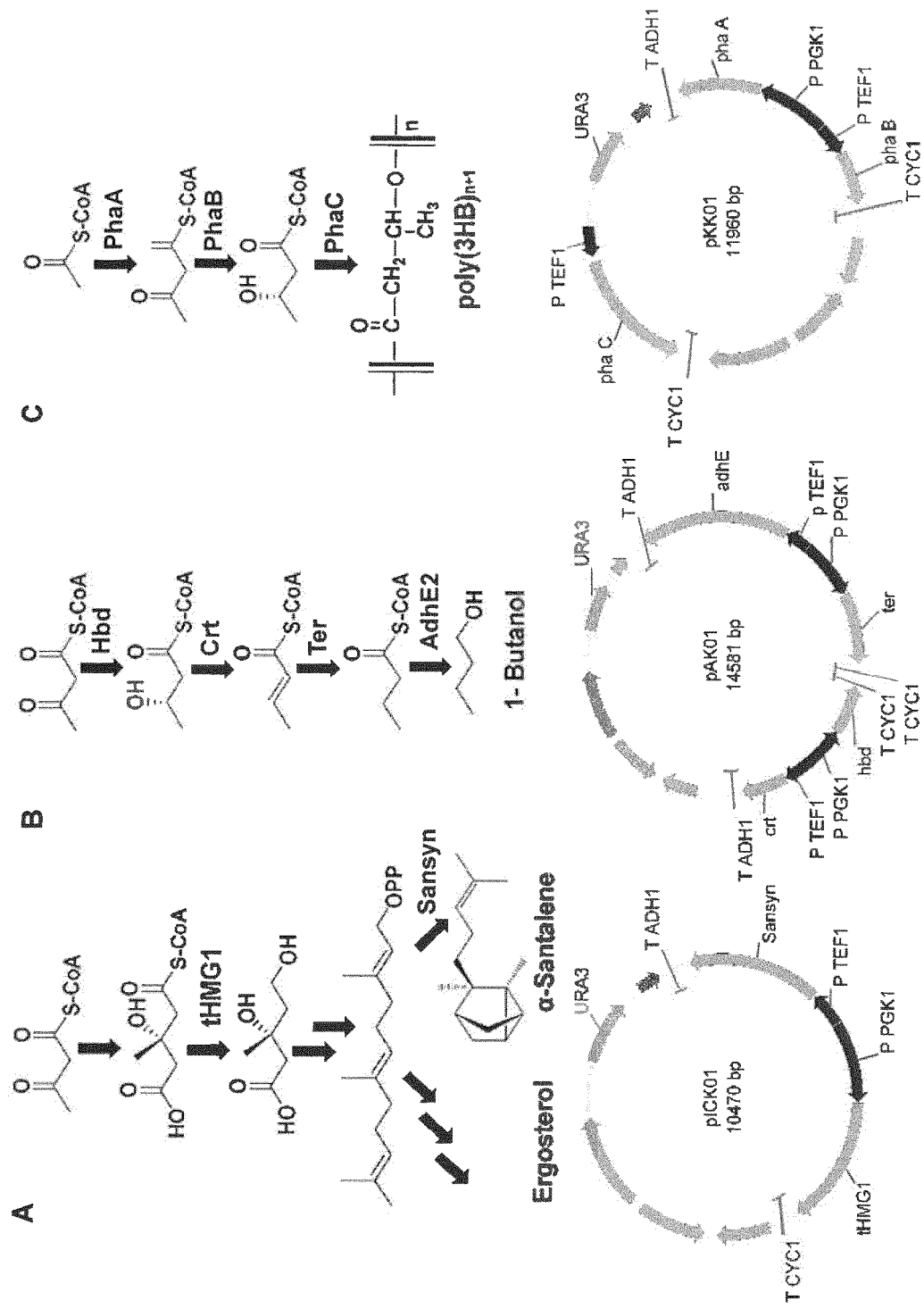
FIG. 4: Map of plasmids pICK01, pAK01 and pPHB-pha and schematic representations of the α-santalene (A), 1-butanol (B) and PHB (C) reconstituted biosynthetic pathways.

To construct the (+)-α santalene expression vector, the santalene synthase (Sts) cDNA (SEQ ID NO: 46) was amplified by PCR from plasmid Cont2B-27-pET101 (WO 2009109597, GenBank accession number: HQ452480), using primers 19 and 20, cut with NotI/PacI and ligated into NotI/PacI restricted vector pSP-G1 (Yeast 2010, 27:954). Subsequently, tHMG1 was PCR amplified using genomic DNA of S. cerevisiae CEN.PK113-5D as template and primers 31 and 32, cut with BamHI/NheI and ligated into the same vector after restriction with BamHI and NheI (Nature 2006, 440:940). This resulted in formation of the expression plasmid pICK01 (FIG. 4).

Example 4

Construction of a Polyhydroxybutyrate Pathway Expression Vector

The polyhydroxybutyrate biosynthesis pathway was introduced into S. cerevisiae strain CEN.PK 113-11C by using a multi-copy plasmid. The biosynthesis pathway of PHB involves three enzymes, β-ketothiolase encoded by phaA, acetoacetyl-CoA reductase encoded by phaB and PHA synthase encoded by the phaC gene. PhaA (SEQ ID NO: 53), phaB (SEQ ID NO: 54) and phaC (SEQ ID NO: 55) were synthesized and codon optimized for expression in S. cerevisiae by DNA 2.0 based on the sequences of the original pha genes from Ralstonia eutropha H16. PhaA and phaB were cloned into the SacI/SpeI and SalI/BamHI sites of pSP-GM2 plasmid downstream of the PGK1 and TEF1 promoter, respectively, to yield pSP-GM2-phaAB. PhaC was cloned into the XhoI/KpnI sites of pSP-GM2 downstream of the TEF1 promoter. The fragment of phaC, TEF1 promoter and CYC1 terminator was amplified using primer 13 and 14 and ligated to pSP-GM2-phaAB at the MfeI site, resulting in plasmid pPHB-pha (FIG. 4).

Example 5

Construction of Butanol Pathway Expression Vectors

Two plasmids were used to express the butanol pathway genes. Four of the genes encoding butyraldehyde dehydrogenase, 3-hydroxybutyryl-CoA dehydrogenase, crotonase and trans enoyl-CoA reductase were expressed from one plasmid, while the thiolase gene (ERG10) was expressed from another plasmid.

ERG10 from CEN.PK113-5D was cloned from pIYC07 into pIYC04 under the TEF1 promoter using SpeI and SacI to yield pCS01.

Genes encoding butyraldehyde dehydrogenase/butanol-dehydrogenase (adhE2), 3-hydroxybutyryl-CoA dehydrogenase (hbd) and crotonase (crt) were from *Clostridium beijerinckii*. Trans enoyl-CoA reductase (ter) was from *Treponema denticola*. All these genes were codon-optimized for high levels of expression in yeast and synthesized by DNA 2.0.

AdhE2 (SEQ ID NO: 50) was cloned into pSP-GM1 using NodI and PadI under a TEF1 promoter. Ter (SEQ ID NO: 51) was then cloned into the same plasmid under a PGK1 promoter using BamHI and NheI. This resulted in the plasmid pAK0.

Crt (SEQ ID NO: 48) was cloned into pSP-GM1 using NodI and PadI under a TEF1 promoter and hbd (SEQ ID NO: 47) was then cloned into the same plasmid under a PGK1 promoter using BamHI and NheI. A cassette containing both of these genes and their promoters was then amplified from this plasmid using primers 15 and 16, which contained Kpn2I and MreI restriction sites. This cassette was then cloned into pAK0, yielding pAK1 (FIG. 4).

Example 6

Deletion of cit2 and mls1

Gene deletion was performed using a cloning-free PCR-based allele replacement method (*Genome Res.* 1997, 7:1174). For deletion of cit2 (SEQ ID NO: 44), the 5' and 3' regions of the cit2 open reading frame were individually amplified from genomic DNA of CEN.PK 113-5D by PCR, using the following oligonucleotides: CIT2-UP-forward, CIT2-UP-reverse, CIT2-DOWN-forward, CIT2-DOWN-reverse (see Table 4 for the list of primers used for gene deletions). The KanMX expression module was amplified in two overlapping parts from the plasmid pUG6 (Guldener et al., 1996), using the oligonucleotides: KanMX-UP-forward, KanMX-UP-reverse, KanMX-DOWN-forward, KanMX-DOWN-reverse.

TABLE 4

List of primers used in this study for citO2 and mls1 deletions (SEQ ID NO: 21 to 32)

| Primers | Sequence (from 5' to 3') |
|---|---|
| CIT2-UP-F | ACCGTCTTATTTACACTCCG |
| CIT2-UP-R | <u>GATCCCCGGGAATTGCCATG</u>TGTTGATATTGTTCCCTGAA |
| CIT2-DW-F | <u>GCAGGGATGCGGCCGCTGAC</u>CTACTTTTACACCCCTCTGC |
| CIT2-DW-R | TGATACTAACCTGACCCCTC |
| MLS1-UP-F | ATTCCCGCAGGGTAATAAA |
| MLS1-UP-R | <u>GATCCCCGGGAATTGCCATG</u>GATGATAGGAGCCCGAGTC |
| MLS1-DW-F | <u>GCAGGGATGCGGCCGCTGAC</u>TGCTTCGTTTCGTAGTTAG |
| MLS1-DW-R | CTGGTGGTCTGTGGTTGTA |
| KanMX-UP-F | <u>CATGGCAATTCCCGGGGATC</u>AAGCTTCGTACGCTGCAGGTCG |
| KanMX-UP-R | CCATGAGTGACGACTGAATCCGG |
| KanMX-DW-F | GCAAAGGTAGCGTTGCCAATG |
| KanMX-DW-R | <u>GTCAGCGGCCGCATCCCTGCC</u>GACTCACTATAGGGAGACCG |

The underlined sequences correspond to the overlapping nucleotides.

Fragments CIT2-UP/KanMX-UP and KanMX-DOWN/CIT2 DOWN were fused to each other via PCR. The two fusion fragments were integrated into the genome by homologous recombination. For the loop-out of the KanMX expression module, procedures were followed as described previously (Guldener et al., 1996). Subsequently, correct transformants were re-streaked on a medium containing 5-fluoroorotic acid for the loop out of the plasmid pSH47 with URA3 marker and the reuse of uracil auxotrophy. Thus, strain SCIYC06 (MATa MAL2-8$^c$ SUC2 ura3-52 cit2Δ::lox) was obtained.

The same approach was used for MLS1 (SEQ ID NO: 45) deletion. The oligonucleotides used to perform MLS1 gene deletions are listed in Table 4.

The deletion of each gene was verified by diagnostic PCR, which was performed by using the genomic DNA from each strain as template, and for each gene two pairs of primers were used, one outside of the integration locus and one inside the integrated fragment. All the primers used for strain confirmation are listed in Table 5.

TABLE 5

List of primers used in this study for strain confirmation (SEQ ID NO: 33 to 40)

| Primers | Sequence (from 5' to 3') |
|---|---|
| CIT2-UP-O | AACCAAACTACGGCATAC |
| CIT2-UP-I | CTGAGCGAGACGAAATAC |
| CIT2-DW-I | CTGCCTCGGTGAGTTTTC |
| CIT2-DW-O | AGGAGCGTTCATCTTGGT |
| MLS1-UP-O | CATCATTCAACTTTCCTCA |
| MLS1-UP-I | CTCAGTGGCAAATCCTAA |
| MLS1-DW-I | AGACTAAACTGGCTGACG |
| MLS1-DW-O | TTCTTATACATTTCCTGACTG |

Finally, strain SCIYC32 (MATa SUC2 MAL2-8$^c$ ura3-52 his3-Δ1 cit2Δ) was constructed by crossing the strain SCIYC06 (MATa SUC2 MAL2-8$^c$ ura3-52 cit2Δ) and CEN.PK110-10C (MATα SUC2 MAL2-8$^c$ his3-Δ1, kindly provided by P. Kötter) followed by tetrad dissection. Similarly, strain SCIYC33 (MATa SUC2 MAL2-8$^c$ ura3-52 his3-Δ1 mls1Δ) was constructed by crossing the strain SCIYC07 (MATa SUC2 MAL2-8$^c$ ura3-52 mls1Δ) and CEN.PK110-10C) followed by dissection.

Example 7

Construction of the Engineered Yeast Strains for α-Santalene, 1-Butanol and PHB Production All yeast strains transformation was performed by the standard lithium acetate method (*Nucleic Acids Res.* 1992, 20:1425). Three to ten colonies from each transformation were screened for the selection of the best producing transformant.

The α-santalene producing strain SCIYC40 was constructed by transforming plasmids pICK01 and pIYC04 into strain CEN.PK113-11C followed by selection on SD-URA-HIS plates. Plasmids pICK01 and pIYC08 were co-transformed into strain CEN.PK113-11C and selected on SD-URA-HIS plates for the construction of SCIYC42. Similarly, these two plasmids were co-transformed into SCIYC32 and SCIYC33 resulting in SCIYC45 and SCIYC46, respectively.

The 1-butanol producing strains pAKY1, pAKY2 and pAKY3 were constructed by transforming CEN.PK113-11C, SCIYC33 and SCIYC32 (respectively) with pIYC08 and pAK1. Strains pAKY4, pAKY5 and pAKY6 were constructed by transforming CEN.PK113-11C, SCIYC33 and SCIYC32 (respectively) with pCS01 and pAK1. Strain pAKY0 was constructed by transforming CEN.PK113-11C with pIYC04 and pAK1. Strains were selected on SD-URA-HIS plates.

The PHB producing strain SCKK005 was constructed by transforming plasmids pPHB-pha and pIYC04 into strain CEN.PK113-11C followed by selection on SD-URA-HIS plates as control. Plasmids pPHB-pha and pIYC08 were co-transformed into strain CEN.PK113-11C for the construction of SCKK006. Similarly, these two plasmids were co-transformed into SCIYC32 and SCIYC33 resulting in SCKK009 and SCKK010, respectively.

Example 8

Methods for the Production, Purification and Quantitative Analysis of α-Santalene, 1-Butanol and PHB To test α-santalene, 1-butanol and PHB production from the different strains described above, 20 mL cultures were started in a 100 ml unbaffled flask by inoculating an amount of pre-culture that resulted in a final optical density of 0.02 at 600 nm ($OD_{600}$). The strains were grown at 30° C. with 180 r.p.m. orbital shaking in defined minimal medium with the following composition: 7.5 g/L $(NH_4)_2SO_4$; 14.4 g/L $KH_2PO_4$; 0.5 g/L $MgSO_4.7H_2O$; 2 ml/L trace metal solution (per liter, pH 4.0: EDTA (sodium salt), 15.0 g; $ZnSO_4.7H_2O$, 0.45 g; $MnCl2.2H_2O$, 1 g; $CoCl_2.6H_2O$, 0.3 g; $CuSO_4.5H_2O$, 0.3 g; $Na_2MoO_4.2H_2O$, 0.4 g; $CaCl_2.2H_2O$, 0.45 g; $FeSO_4.7H_2O$, 0.3 g; $H_3BO_3$, 0.1 g and KI, 0.10 g). The pH of mineral medium was adjusted to 6.5 by adding 2 M NaOH and autoclaved separately from the carbon source solution. The glucose was added at the concentration of 20 g/L. Vitamin solution (per liter, pH 6.5: biotin, 0.05 g; p-amino benzoic acid, 0.2 g; nicotinic acid, 1 g; Ca-pantothenate, 1 g; pyridoxine-HCl, 1 g; thiamine-HCl, 1 g and myo-inositol, 25 g) was filter sterilized and aseptically added to the medium after autoclaving at the concentration of 1 ml/L. To prepare the pre-cultures, culture tubes containing 5 mL of defined medium (as described above) were inoculated with a single colony of strains of interest. These inocula were cultured at 30° C. with 220 r.p.m. orbital shaking to an $OD_{600}$ between 1 and 2.

For the production of α-santalene, 10% (v/v) dodecane was added to the main culture at an $OD_{600}$ of 1 to capture α-santalene in the organic phase. This dodecane layer was sampled and diluted in decane for the determination of α-santalene production by GC-MS.

α-Santalene was analyzed by gas chromatography-mass spectrometry (Thermo Scientific, Waltham, Mass.) equipped with a SLB-5 ms capillary column (30 m, 0.25 mm i.d., 0.25 μm film thickness; Supelco, Bellefonte, Pa., USA). The carrier gas was helium at a constant flow of 1.2 ml/min. A split/splitless injector was used in the splitless mode. The initial oven temperature was 80° C. and the injector temperature was 250° C. The oven temperature was increased to 120° C. at a rate of 10° C./min and subsequently increased to 160° C. at a rate of 3° C./min. Then the temperature ramped by a gradient of 10° C./min to 270° C. and held for 5 mM at this temperature. Full mass spectra were generated by scanning m/z range within 50-650 for metabolite identification. Quantification of α-santalene was carried out using standard curves.

PHB was analyzed as described previously (*Appl. Environ. Microbiol.* 1983, 46: 1339; *Appl. Environ. Microbiol.* 2006, 72:3412). More than 10 mg of cells was collected from culture by centrifugation (10 min, 5000×g). The resulting cell pellet was washed once and lyophilized. The dry cells were boiled in 1 ml of concentrated sulfuric acid for 60 min and then diluted with 4 ml of 14 mM $H_2SO_4$. Samples were centrifuged (15 mM, 16,000×g) to remove cell debris, and the supernatant was analyzed by high pressure liquid chromatography (Dionex-HPLC, Sunnyvale, Calif.) equipped with an Aminex HPX-87H ion exclusion column (300×7.8 mm; Bio-Rad Hercules, Calif.) and UV detector. Commercially available PHB (Sigma-Aldrich, St Louis, Mo.), processed in parallel with the samples, was used as a standard. The HPLC was operated at 60° C. and a flow rate of 0.6 ml/min of 5 mM $H_2SO_4$.

To analyze 1-butanol levels, samples at different time points were collected, centrifuged and filtered. Samples were then analyzed by high pressure liquid chromatography (Dionex-HPLC, Sunnyvale, Calif.) equipped with an Aminex HPX-87H ion exclusion column (300×7.8 mm; Bio-Rad Hercules, Calif.) and RI detector. Commercially available 1-butanol, was used as a standard. The HPLC was operated at 45° C. and a flow rate of 0.6 ml/min of 5 mM $H_2SO_4$.

Example 9

Evaluation of the Acetyl-CoA Platform Strain

Figure 5A:
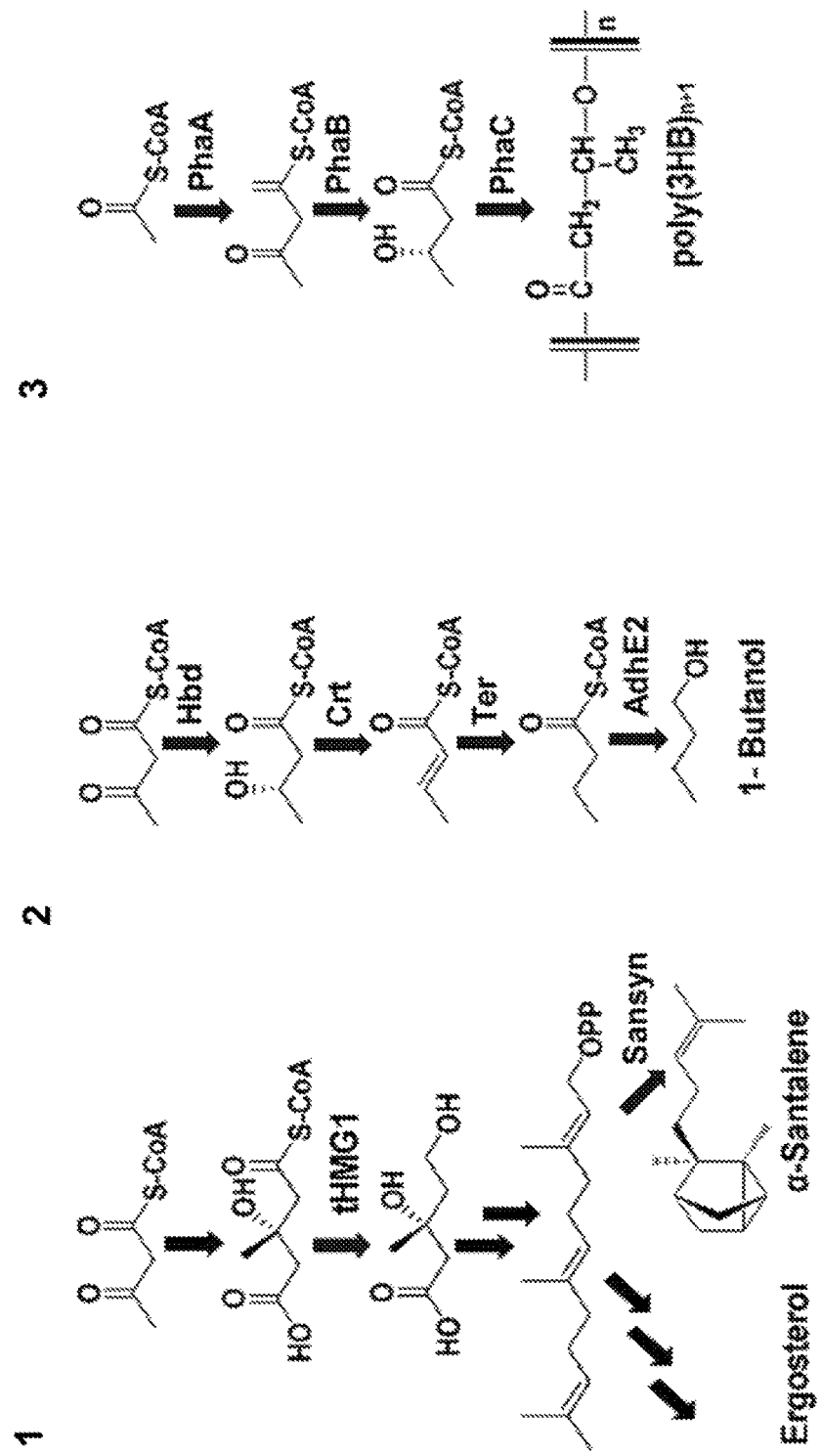
Figure 6:
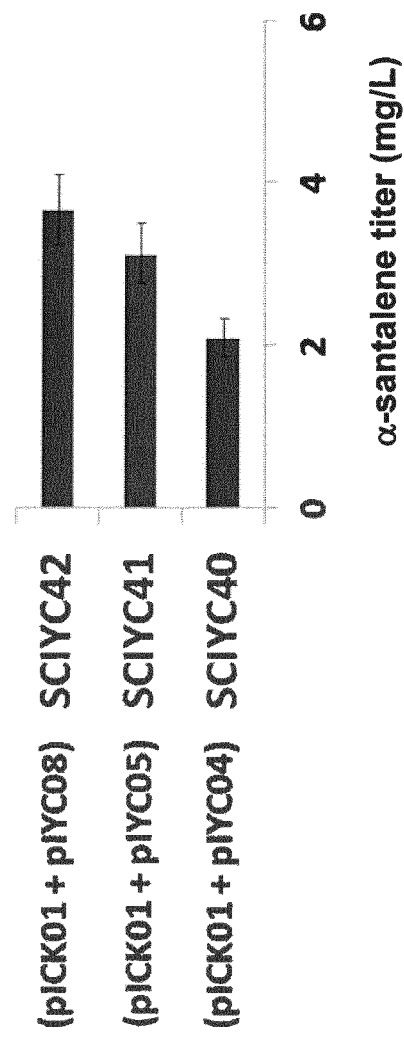
FIG. 6: Overexpression of Adh2 and Erg10 further improves α-santalene titers in yeast cells co-expressing $ACS_{SE}$ and ALD6. Comparison of α-santalene accumulation in yeast strains expressing: (i) a truncated version of the hydroxymethylglutaryl-CoA reductase (tHMG1) gene and a α-santalene synthase gene (Sts) (strain SCIYC40); (ii) the tHMG1 and Sts genes together with the $ACS_{SE}$ and ALD6 genes (strain SCIYC41); the tHMG1, Sts, $ACS_{SE}$, ALD6 genes together with Adh2 and Erg10 (strain SCIY42).

In order to evaluate the acetyl-CoA platform strain, the production of α-santalene, which is a naturally occurring sesquiterpene and the biosynthetic precursor of α-santalol, an important constituent of sandalwood oil was evaluated. As shown in FIG. 4A, santalene is derived directly in a single enzymatic step from farnesyl diphosphate (FPP), the biological precursor for sesquiterpenes. To increase the FPP production, the yeast endogenous mevalonate pathway was deregulated by overexpression of the catalytic domain of 3-hydroxy-3-methylglutaryl-coenzyme A reductase 1 (tHMG1) (*J Biol Chem* 1999, 274:316171), previously demonstrated to result in an improvement of isoprenoid production in yeast (*Nature* 2006, 440:940). To overcome the difficulties in expressing the plant genes in yeast, the Sts cDNA encoding α-santalene synthase was codon-optimized for high level expression in *S. cerevisiae*. The transgenic yeast strain SCYC040 (Table 1), as reference strain, was transformed with the plasmid pICK01 containing tHMG1 and Sts. In a shake-flask culture, 2.08 mg/L α-santalene was produced after 48 h of growth (FIGS. 5A1 and 5B1). By co-expressing pICK01 with plasmid pIYC08 expressing ALD6, $ACS_{SE}$, ADH2 and ERG10, α-santalene production was increased to 3.65 mg/L (FIGS. 5A1 and 5B1, strain SCYC042). Combining the CIT2 deletion and co-expression with plasmid pIYC08 resulted in strain SCYC045 able to produce 4.98 mg/L α-santalene (FIGS. 5A1 and B1). Furthermore, when plasmid pIYC08 was co-expressed in an MLS1 deletion strain resulting in strain SCYC046, α-santalene production was further increased to 8.29 mg/L (FIGS. 5A1 and 5B1), which represent a 4-fold improvement compared to the reference strain. To evaluate further the current strategy and compare it with previous published work on overexpression of $ACS_{SE}$ and ALD6 (*Metab Eng* 2007, 9:160), these two genes were co-expressed with plasmid pICK01 (FIG. 6, strain SCIYC41). The results showed that additional over-expression of ADH2 and ERG10 leads to a 25% increase in α-santalene final titers (FIG. 6, strain SCIYC42) and together with the block strategy, a 2 to 4-fold increase in α-santalene production was achieved (FIG. 6).

Figure 2:
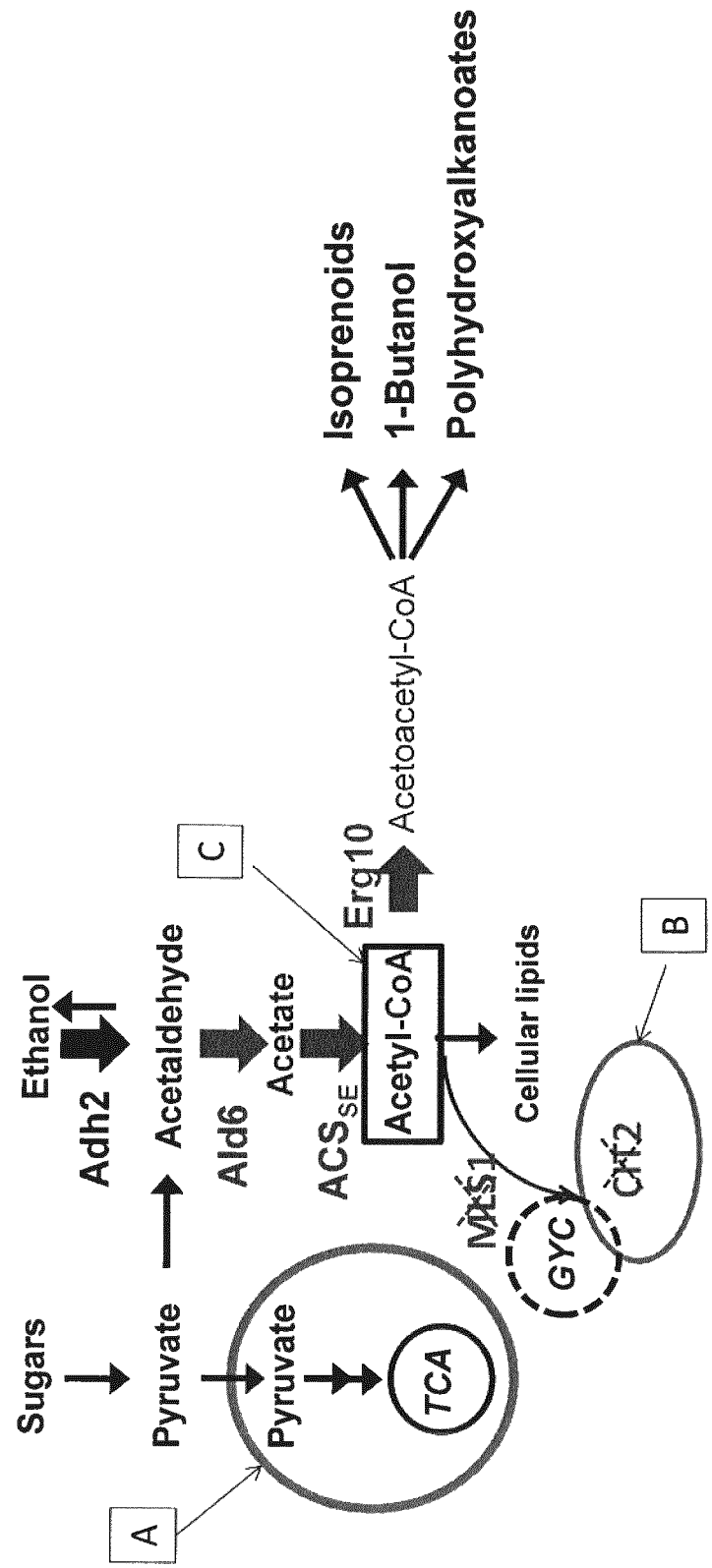
FIG. 2: Illustration of the push-pull-block metabolic engineering strategy for improving the production of acetyl-CoA in the cytosol (the 3 cellular compartments where acetyl-CoA is localized are depicted as in FIG. 1). By over-expressing the endogenous ALD6, encoding NADP-dependent acetaldehyde dehydrogenase, and the heterologous ACS variant from *Salmonella enterica* ($ACS_{SE}$), encoding acetyl-CoA synthase, it is ensured that flux is directed from acetaldehyde to acetyl-CoA in the cytosol (the push part of the strategy). Through further over-expression of ADH2, encoding alcohol dehydrogenase, it is further ensured that ethanol produced can be converted back to acetaldehyde and from here further to acetyl-CoA (the pull part of the strategy). To pull acetyl-CoA in the direction of desirable pathways we over-expressed ERG10 encoding acetoacetyl-CoA synthase that catalyzes the conversion of acetyl-CoA to acetoacetyl-CoA (AcAcCoA), as this metabolite is a common precursor for the three products used to evaluate the acetyl-CoA platform strain. Besides the over-expression, reactions that involve consumption of acetyl-CoA were deleted (the block part of the strategy). This involves two key reactions of the glyoxylate cycle (GYC), namely peroxisomal citrate synthase, encoded by CIT2, and cytosolic malic synthase, encoded by MLS1. The pathway map in the figure is a simplified view of metabolism, e.g. acetyl-CoA used by citrate synthase in the peroxisome is synthesized there by Acs1p from acetate.

Next, the production of 1-butanol was evaluated in the acetyl-CoA platform strain. 1-Butanol has been generally considered as a possible gasoline replacement, because it has higher energy density while it is less corrosive and less water soluble than ethanol (*Nat Chem Biol* 2011, 11:262). The reactions and corresponding enzymes needed for 1-butanol production from acetyl-CoA are outlined in FIG. 4B. The synthetic pathway was assembled by choosing a 3-hydroxy-butyryl-CoA dehydrogenase (Hbd) that utilizes NADH as a cofactor, a crotonase (Crt) and a bifuntional butyraldehyde and butanol dehydrogenase (AdhE2) from *Clostridium beijerinckii* (*Microb Cell Fact* 2008, 7:8), and a NADH-dependent crotonyl-CoA specific trans-enoyl-CoA reductase (Ter) from *Treponema denticola* (*Nat Chem Biol* 2011, 7:222). The genes encoding these enzymes were chemically synthesized to be codon-optimized and cloned into one episomal plasmid, yielding 1-butanol production plasmid pAK01 (FIG. 4B). To check the capability of the assembled pathway for producing 1-butanol, *S. cerevisiae* cultures expressing these exogenous genes were grown in minimal media with 2% glucose. 2.17 mg/L of 1-butanol were observed (FIG. 4B, strain SCAK00) which is similar to the amounts previously produced in *S. cerevisiae* (21). The functional pathway was then simultaneously co-expressed with plasmid pIYC08 harboring ALD6, $ACS_{SE}$, ADH2 and ERG10 (FIGS. 5A2 and 5B2, strain SCAK01), and a titer of 1-butanol of 9.40 mg/L was reached, which is a ~4-fold increase over the reference strain without engineering of the acetyl-CoA pathway (FIGS. 5A2 and 5B2). These results demonstrate that it is important to ensure efficient provision of the precursor acetyl-CoA for butanol production. Further evaluation of this two-plasmid system in a MLS1 deletion strain (FIGS. 5A2 and 5B2, strain SCAK02) resulted in an additional 1.7-fold increase in 1-butanol production to 14.04 mg/L. When combining over-expression with CIT2 deletion resulted in a strain (FIGS. 5A2 and 5B2, strain SCAK03) able to produce 16.26 mg/L 1-butanol, the production level is nearly 8-fold higher than previously reported (*Microb Cell Fact* 2008, 7:8).

The acetyl-CoA platform strain was finally examined for the production of PHB, a member of a family of commercially interesting biodegradable biopolymers (*Microbiol Mol Biol Rev* 1999, 63:21). For production of PHB in *S. cerevisiae*, the synthetic pathway was implemented by transformation of a three-gene pathway from *Ralstonia eutropha* for monomer biosynthesis (phaA and phaB) and polymerization (PhaC) (*J Biol Chem* 1989, 264:15293; *J Biol Chem* 1989, 264:15298; *J Biotechnol* 2006, 124:561). The synthetic, codon-optimized genes encoding phaA, pHaB and phaC were cloned into a single expression vector, resulting in pPHB-pha (FIG. 4C). Expression of the synthetic pathway in the reference strain resulted in a PHB concentration of 13.39 mg/L after 120 h of growth in defined minimal medium (FIGS. 5A3 and 5B3, strain SCKK005). When plasmid pIYC08 including ALD6, $ACS_{SE}$, ADH2 and ERG10 was co-expressed with the PHB production vector, PHB accumulated to 240.99 mg/L, representing an 18-fold increase compared to the reference strain (FIGS. 5A3 and 5B3, strain SCKK006) (*J Biotechnol* 2006, 124:561). Simultaneous co-expression of these two plasmids in a strain with either CIT2 deletion or MLS1 deletion did, however, not improve PHB production further, showing that the block strategy does not work for production of PHB (FIGS. 5A3 and 5B3, strain SCKK09 and SCKK10). This is likely due to the fact that in the batch fermentations used here to evaluate PHB production, the PHB is mainly produced in the ethanol phase of the diauxic shift. The strains carrying deletions of CIT2 or MLS1 are unable to grow on a $C_2$ compound such as ethanol and acetate as sole carbon source, and these strains can therefore not provide the necessary Gibbs free energy and redox equivalents for PHB production in the ethanol growth phase.

What is claimed is:

1. A yeast cell modified by overexpression of an aldehyde dehydrogenase, and an acetyl-CoA synthetase (ACS), an alcohol dehydrogenase and an acetoacetyl-CoA synthase, and characterized in that a gene encoding a peroxisomal citrate synthase or a gene encoding a cytosolic malate synthase has been deleted from the yeast cell genome.

2. The yeast cell of claim 1, wherein the yeast cell is a *Saccharomyces cerevisiae* cell.

3. The yeast cell of claim 2, wherein the aldehyde dehydrogenase is ALD6, the alcohol dehydrogenase is ADH2, the acetoacetyl-CoA synthase is ERG10, the peroxisomal citrate synthase is CIT2 and the cytosolic malate synthase is MLS1.

4. The yeast cell of claim 1, wherein the ACS contains a point mutation that prevents the enzyme from being inhibited by acetylation.

5. The yeast cell of claim 4, wherein the ACS is the variant L641P from *Salmonella enterica*.

6. A method of making a modified yeast cell comprising over-expressing an aldehyde dehydrogenase, an acetyl-CoA synthase (ACS), an alcohol dehydrogenase and an acetoacetyl-CoA synthase in a yeast cell, and deleting a gene encoding a peroxisomal citrate synthase or a gene encoding a cytosolic malate synthase from the yeast cell genome.

7. The method of claim 6, wherein the yeast cell is a *Saccharomyces cerevisiae* cell.

8. The method of claim 7, wherein the aldehyde dehydrogenase is ALD6, the alcohol dehydrogenase is ADH2, the acetoacetyl-CoA synthase is ERG10, the peroxisomal citrate synthase is CIT2 and the cytosolic malate synthase is MLS1.

9. The method of claim 6, wherein the ACS contains a point mutation that prevents the enzyme from being inhibited by acetylation.

10. A method for producing increased levels of a product selected from the group consisting of a terpenoid, a fatty acid, 1-butanol and polyhydroxy butyrate derived from acetyl-CoA or acetoacetyl-CoA comprising (a) culturing the yeast cell of claim 1, which is capable of producing a product selected from the group consisting of a terpenoid, a fatty acid, 1-butanol and polyhydroxy butyrate, under conditions conducive to the production of said product, (b) producing a product selected from the group consisting of a terpenoid, a fatty acid, 1-butanol and polyhydroxy butyrate; and (c) optionally, isolating the product produced in step (b).

11. The method of claim 10, wherein the terpenoid is—α-santalene.

* * * * *

SEQUENCE LISTING

<160> NUMBER OF SEQ ID NOS: 55

<210> SEQ ID NO 1
<211> LENGTH: 37
<212> TYPE: DNA
<213> ORGANISM: Artificial
<220> FEATURE:
<223> OTHER INFORMATION: Primer

<400> SEQUENCE: 1
cgccggatcc aaaacaatga ctaagctaca ctttgac          37

<210> SEQ ID NO 2
<211> LENGTH: 31
<212> TYPE: DNA
<213> ORGANISM: Artificial
<220> FEATURE:
<223> OTHER INFORMATION: Primer

<400> SEQUENCE: 2
cgcgctcgag ttacaactta attctgacag c          31

<210> SEQ ID NO 3
<211> LENGTH: 34
<212> TYPE: DNA
<213> ORGANISM: Artificial
<220> FEATURE:
<223> OTHER INFORMATION: Primer

<400> SEQUENCE: 3
tattaggccg gccccgtgga aatgaggggt atgc          34

<210> SEQ ID NO 4
<211> LENGTH: 37
<212> TYPE: DNA
<213> ORGANISM: Artificial
<220> FEATURE:
<223> OTHER INFORMATION: Primer

<400> SEQUENCE: 4
ggccggcgga tcctttttga ttaaaattaa aaaaact          37

<210> SEQ ID NO 5
<211> LENGTH: 37
<212> TYPE: DNA
<213> ORGANISM: Artificial
<220> FEATURE:
<223> OTHER INFORMATION: Primer

<400> SEQUENCE: 5
gcgcggatcc aaaacaatgt ctattccaga aactcaa          37

<210> SEQ ID NO 6
<211> LENGTH: 30
<212> TYPE: DNA
<213> ORGANISM: Artificial
<220> FEATURE:
<223> OTHER INFORMATION: Primer

<400> SEQUENCE: 6
gcgatccgga acgtcaagac gaaaagtgaa          30

<210> SEQ ID NO 7
<211> LENGTH: 37
<212> TYPE: DNA
<213> ORGANISM: Artificial
<220> FEATURE:
<223> OTHER INFORMATION: Primer

<400> SEQUENCE: 7
gccgcgacta gtaaaacaat gtctcagaac gtttaca          37

<210> SEQ ID NO 8
<211> LENGTH: 34
<212> TYPE: DNA
<213> ORGANISM: Artificial

```
<220> FEATURE:
<223> OTHER INFORMATION: Primer

<400> SEQUENCE: 8
gcggcccgag ctctcatatc ttttcaatga caat                         34

<210> SEQ ID NO 9
<211> LENGTH: 29
<212> TYPE: DNA
<213> ORGANISM: Artificial
<220> FEATURE:
<223> OTHER INFORMATION: Primer

<400> SEQUENCE: 9
ctatcttccg gagcacacac catagcttc                               29

<210> SEQ ID NO 10
<211> LENGTH: 33
<212> TYPE: DNA
<213> ORGANISM: Artificial
<220> FEATURE:
<223> OTHER INFORMATION: Primer

<400> SEQUENCE: 10
tctaaacgcc ggcgaattgg agcgacctca tgc                          33

<210> SEQ ID NO 11
<211> LENGTH: 29
<212> TYPE: DNA
<213> ORGANISM: Artificial
<220> FEATURE:
<223> OTHER INFORMATION: Primer

<400> SEQUENCE: 11
aaactcctag gccgtggaaa tgaggggta                               29

<210> SEQ ID NO 12
<211> LENGTH: 31
<212> TYPE: DNA
<213> ORGANISM: Artificial
<220> FEATURE:
<223> OTHER INFORMATION: Primer

<400> SEQUENCE: 12
gtcaaaggcg cgccacgtca agacgaaaag t                            31

<210> SEQ ID NO 13
<211> LENGTH: 35
<212> TYPE: DNA
<213> ORGANISM: Artificial
<220> FEATURE:
<223> OTHER INFORMATION: Primer

<400> SEQUENCE: 13
tacaattgct attattatcc tgctcagtgg tactt                        35

<210> SEQ ID NO 14
<211> LENGTH: 32
<212> TYPE: DNA
<213> ORGANISM: Artificial
<220> FEATURE:
<223> OTHER INFORMATION: Primer

<400> SEQUENCE: 14
tccaattgtc agtgagcgag gaagcggaag ag                           32
```

<210> SEQ ID NO 15
<211> LENGTH: 36
<212> TYPE: DNA
<213> ORGANISM: Artificial
<220> FEATURE:
<223> OTHER INFORMATION: Primer

<400> SEQUENCE: 15
gaagaacgcc ggcggagcga cctcatgcta tacctg                36

<210> SEQ ID NO 16
<211> LENGTH: 33
<212> TYPE: DNA
<213> ORGANISM: Artificial
<220> FEATURE:
<223> OTHER INFORMATION: Primer

<400> SEQUENCE: 16
gttgtttccg gatgttacat gcgtacacgc gtc                   33

<210> SEQ ID NO 17
<211> LENGTH: 62
<212> TYPE: DNA
<213> ORGANISM: Artificial
<220> FEATURE:
<223> OTHER INFORMATION: Primer

<400> SEQUENCE: 17
gaacaacagc tggataaagg cgcgccaaac gacctaggaa ttggagcgac ctcatgctat      60
ac                                                                    62

<210> SEQ ID NO 18
<211> LENGTH: 60
<212> TYPE: DNA
<213> ORGANISM: Artificial
<220> FEATURE:
<223> OTHER INFORMATION: Primer

<400> SEQUENCE: 18
gaacaacagc tggataaacg ccggcgaaac gatccggagg atcttcgagc gtcccaaaac      60

<210> SEQ ID NO 19
<211> LENGTH: 45
<212> TYPE: DNA
<213> ORGANISM: Artificial
<220> FEATURE:
<223> OTHER INFORMATION: Primer

<400> SEQUENCE: 19
gttgttgcgg ccgcaaaaca atgtcaactc aacaagtttc atcag                     45

<210> SEQ ID NO 20
<211> LENGTH: 35
<212> TYPE: DNA
<213> ORGANISM: Artificial
<220> FEATURE:
<223> OTHER INFORMATION: Primer

<400> SEQUENCE: 20
gttgttttaa ttaactaatc gtcaagctta acggg                                35

<210> SEQ ID NO 21
<211> LENGTH: 20
<212> TYPE: DNA
<213> ORGANISM: Artificial

<220> FEATURE:
<223> OTHER INFORMATION: Primer

<400> SEQUENCE: 21
accgtcttat ttacactccg                                              20

<210> SEQ ID NO 22
<211> LENGTH: 40
<212> TYPE: DNA
<213> ORGANISM: Artificial
<220> FEATURE:
<223> OTHER INFORMATION: Primer

<400> SEQUENCE: 22
gatccccggg aattgccatg tgttgatatt gttccctgaa                        40

<210> SEQ ID NO 23
<211> LENGTH: 40
<212> TYPE: DNA
<213> ORGANISM: Artificial
<220> FEATURE:
<223> OTHER INFORMATION: Primer

<400> SEQUENCE: 23
gcagggatgc ggccgctgac ctacttttac acccctctgc                        40

<210> SEQ ID NO 24
<211> LENGTH: 20
<212> TYPE: DNA
<213> ORGANISM: Artificial
<220> FEATURE:
<223> OTHER INFORMATION: Primer

<400> SEQUENCE: 24
tgatactaac ctgacccctc                                              20

<210> SEQ ID NO 25
<211> LENGTH: 19
<212> TYPE: DNA
<213> ORGANISM: Artificial
<220> FEATURE:
<223> OTHER INFORMATION: Primer

<400> SEQUENCE: 25
attcccgcag ggtaataaa                                               19

<210> SEQ ID NO 26
<211> LENGTH: 39
<212> TYPE: DNA
<213> ORGANISM: Artificial
<220> FEATURE:
<223> OTHER INFORMATION: Primer

<400> SEQUENCE: 26
gatccccggg aattgccatg gatgatagga gcccgagtc                         39

<210> SEQ ID NO 27
<211> LENGTH: 39
<212> TYPE: DNA
<213> ORGANISM: Artificial
<220> FEATURE:
<223> OTHER INFORMATION: Primer

<400> SEQUENCE: 27
gcagggatgc ggccgctgac tgcttcgttt cgtagttag                         39

```
<210> SEQ ID NO 28
<211> LENGTH: 19
<212> TYPE: DNA
<213> ORGANISM: Artificial
<220> FEATURE:
<223> OTHER INFORMATION: Primer

<400> SEQUENCE: 28
ctggtggtct gtggttgta                                                    19

<210> SEQ ID NO 29
<211> LENGTH: 42
<212> TYPE: DNA
<213> ORGANISM: Artificial
<220> FEATURE:
<223> OTHER INFORMATION: Primer

<400> SEQUENCE: 29
catggcaatt cccggggatc aagcttcgta cgctgcaggt cg                          42

<210> SEQ ID NO 30
<211> LENGTH: 23
<212> TYPE: DNA
<213> ORGANISM: Artificial
<220> FEATURE:
<223> OTHER INFORMATION: Primer

<400> SEQUENCE: 30
ccatgagtga cgactgaatc cgg                                               23

<210> SEQ ID NO 31
<211> LENGTH: 21
<212> TYPE: DNA
<213> ORGANISM: Artificial
<220> FEATURE:
<223> OTHER INFORMATION: Primer

<400> SEQUENCE: 31
gcaaaggtag cgttgccaat g                                                 21

<210> SEQ ID NO 32
<211> LENGTH: 41
<212> TYPE: DNA
<213> ORGANISM: Artificial
<220> FEATURE:
<223> OTHER INFORMATION: Primer

<400> SEQUENCE: 32
gtcagcggcc gcatccctgc cgactcacta tagggagacc g                           41

<210> SEQ ID NO 33
<211> LENGTH: 18
<212> TYPE: DNA
<213> ORGANISM: Artificial
<220> FEATURE:
<223> OTHER INFORMATION: Primer

<400> SEQUENCE: 33
aaccaaacta cggcatac                                                     18

<210> SEQ ID NO 34
<211> LENGTH: 18
<212> TYPE: DNA
<213> ORGANISM: Artificial
<220> FEATURE:
<223> OTHER INFORMATION: Primer
```

```
<400> SEQUENCE: 34
ctgagcgaga cgaaatac                                                  18

<210> SEQ ID NO 35
<211> LENGTH: 18
<212> TYPE: DNA
<213> ORGANISM: Artificial
<220> FEATURE:
<223> OTHER INFORMATION: Primer

<400> SEQUENCE: 35
ctgcctcggt gagttttc                                                  18

<210> SEQ ID NO 36
<211> LENGTH: 18
<212> TYPE: DNA
<213> ORGANISM: Artificial
<220> FEATURE:
<223> OTHER INFORMATION: Primer

<400> SEQUENCE: 36
aggagcgttc atcttggt                                                  18

<210> SEQ ID NO 37
<211> LENGTH: 19
<212> TYPE: DNA
<213> ORGANISM: Artificial
<220> FEATURE:
<223> OTHER INFORMATION: Primer

<400> SEQUENCE: 37
catcattcaa ctttcctca                                                 19

<210> SEQ ID NO 38
<211> LENGTH: 18
<212> TYPE: DNA
<213> ORGANISM: Artificial
<220> FEATURE:
<223> OTHER INFORMATION: Primer

<400> SEQUENCE: 38
ctcagtggca aatcctaa                                                  18

<210> SEQ ID NO 39
<211> LENGTH: 18
<212> TYPE: DNA
<213> ORGANISM: Artificial
<220> FEATURE:
<223> OTHER INFORMATION: Primer

<400> SEQUENCE: 39
agactaaact ggctgacg                                                  18

<210> SEQ ID NO 40
<211> LENGTH: 21
<212> TYPE: DNA
<213> ORGANISM: Artificial
<220> FEATURE:
<223> OTHER INFORMATION: Primer

<400> SEQUENCE: 40
ttcttataca tttcctgact g                                              21

<210> SEQ ID NO 41
```

<211> LENGTH: 1047
<212> TYPE: DNA
<213> ORGANISM: Saccharomyces cerevisiae

<400> SEQUENCE: 41

```
atgtctattc cagaaactca aaaagccatt atcttctacg aatccaacgg caagttggag        60
cataaggata tcccagttcc aaagccaaag cccaacgaat tgttaatcaa cgtcaagtac       120
tctggtgtct gccacaccga tttgcacgct tggcatggtg actggccatt gccaactaag       180
ttaccattag ttggtggtca cgaaggtgcc ggtgtcgttg tcggcatggg tgaaaacgtt       240
aagggctgga gatcggtga ctacgccggt atcaaatggt tgaacggttc ttgtatggcc        300
tgtgaatact gtgaattggg taacgaatcc aactgtcctc acgctgactt gtctggttac       360
acccacgacg ttctttcca gaatacgct accgctgacg ctgttcaagc cgctcacatt         420
cctcaaggta ctgacttggc tgaagtcgcg ccaatcttgt gtgctggtat caccgtatac       480
aaggctttga gtctgccaa cttgagagca ggccactggg cggccatttc tggtgctgct        540
ggtggtctag ttctttggc tgttcaatat gctaaggcga tgggttacag agtcttaggt        600
attgatggtg gtccaggaaa ggaagaattg tttacctcgc tcggtggtga agtattcatc       660
gacttcacca aagagaagga cattgttagc gcagtcgtta aggctaccaa cggcggtgcc       720
cacggtatca tcaatgtttc cgtttccgaa gccgctatcg aagcttctac cagatactgt       780
agggcgaacg gtactgttgt cttggttggt ttgccagccg gtgcaaagtg ctcctctgat       840
gtcttcaacc acgttgtcaa gtctatctcc attgtcggct cttacgtggg gaacagagct       900
gataccagag aagcccttag atttctttgcc agaggtctag tcaagtctcc aataaaggta      960
gttggcttat ccagtttacc agaaatttac gaaaagatgg agaagggcca aattgctggt      1020
agatacgttg ttgacacttc taaataa                                          1047
```

<210> SEQ ID NO 42
<211> LENGTH: 1503
<212> TYPE: DNA
<213> ORGANISM: Saccharomyces cerevisiae

<400> SEQUENCE: 42

```
atgactaagc tacactttga cactgctgaa ccagtcaaga tcacacttcc aaatggtttg        60
acatacgagc aaccaaccgg tctattcatt aacaacaagt ttatgaaagc tcaagacggt       120
aagacctatc ccgtcgaaga tccttccact gaaaacaccg tttgtgaggt ctcttctgcc       180
accactgaag atgttgaata tgctatcgaa tgtgccgacc gtgcttttca cgacactgaa       240
tgggctaccc aagacccaag agaaagaggc cgtctactaa gtaagttggc tgacgaattg       300
gaaagccaaa ttgacttggt ttcttccatt gaagctttgg acaatggtaa acttttggcc       360
ttagcccgtg gggatgttac cattgcaatc aactgtctaa gagatgctgc tgcctatgcc       420
gacaaagtca acggtagaac aatcaacacc ggtgacggct acatgaactt caccacctta       480
gagccaatcg gtgtctgtgg tcaaattatt ccatggaact ttccaataat gatgttggct       540
tggaagatcg ccccagcatt ggccatgggt aacgtctgta tcttgaaacc cgctgctgtc       600
acacctttaa atgccctata ctttgcttct ttatgtaaga aggttggtat tccagctggt       660
gtcgtcaaca tcgttccagg tcctggtaga actgttggtg ctgctttgac caacgaccca       720
agaatcagaa agctggcttt taccggttct acagaagtcg gtaagagtgt tgctgtcgac       780
tcttctgaat ctaacttgaa gaaaatcact ttggaactag tggtaagtc cgcccatttg        840
gtctttgacg atgctaacat taagaagact ttaccaaatc tagtaaacgg tattttcaag       900
```

```
aacgctggtc aaatttgttc ctctggttct agaatttacg ttcaagaagg tatttacgac    960
gaactattgg ctgcttttcaa ggcttacttg gaaaccgaaa tcaaagttgg taatccattt   1020
gacaaggcta acttccaagg tgctatcact aaccgtcaac aattcgacac aattatgaac   1080
tacatcgata tcggtaagaa agaaggcgcc aagatcttaa ctggtggcga aaaagttggt   1140
gacaagggtt acttcatcag accaaccgtt ttctacgatg ttaatgaaga catgagaatt   1200
gttaaggaag aaattttttgg accagttgtc actgtcgcaa agttcaagac tttagaagaa   1260
ggtgtcgaaa tggctaacag ctctgaattc ggtctaggtt ctggtatcga aacagaatct   1320
ttgagcacag gtttgaaggt ggccaagatg ttgaaggccg gtaccgtctg gatcaacaca   1380
tacaacgatt ttgactccag agttccattc ggtggtgtta agcaatctgg ttacggtaga   1440
gaaatgggtg aagaagtcta ccatgcatac actgaagtaa agctgtcag aattaagttg    1500 taa                                                                 1503

<210> SEQ ID NO 43
<211> LENGTH: 1190
<212> TYPE: DNA
<213> ORGANISM: Saccharomyces cerevisiae

<400> SEQUENCE: 43
atgtctcaga acgtttacat tgtatcgact gccagaaccc caattggttc attccagggt    60
tctctatcct ccaagacagc agtggaattg ggtgctgttg ctttaaaagg cgccttggct   120
aaggttccag aattggatgc atccaaggat tttgacgaaa ttattttttgg taacgttctt   180 tctgccaatt tgggccaagc tccggccaga caagttgctt tggctgccgg tttgagtaat   240
catatcgttg caagcacagt taacaaggtc tgtgcatccg ctatgaaggc aatcattttg   300
ggtgctcaat ccatcaaatg tggtaatgct gatgttgtcg tagctggtgg ttgtgaatct   360
atgactaacg caccatacta catgccagca gcccgtgcgg tgccaaaatt tggccaaact   420
gttcttgttg atggtgtcga agagatgggt tgaacgatg cgtacgatgg tctagccatg   480
ggtgtacacg cagaaaagtg tgcccgtgat tgggatatta ctagagaaca acaagacaat   540
tttgccatcg aatcctacca aaaatctcaa aaatctcaaa aggaaggtaa attcgacaat   600
gaaattgtac ctgttaccat taagggattt agaggtaagc ctgatactca agtcacgaag   660
gacgaggaac ctgctagatt acacgttgaa aaattgagat ctgcaaggac tgttttccaa   720
aaagaaaacg gtactgttac tgccgctaac gcttctccaa tcaacgatgg tgctgcagcc   780
gtcatcttgg tttccgaaaa agttttgaag gaaaagaatt tgaagccttt ggctattatc   840
aaaggttggg gtgaggccgc tcatcaacca gctgatttta catgggctcc atctcttgca   900
gttccaaagg ctttgaaaca tgctggcatc gaagacatca attctgttga ttactttgaa   960
ttcaatgaag ccttttcggt tgtcggtttg gtgaacacta agattttgaa gctagaccca   1020
tctaaggtta atgtatatgg tggtgctgtt gctctaggtc acccattggg ttgttctggt   1080
gctagagtgg ttgttacact gctatccatc ttacagcaag aaggaggtaa gatcggtgtt   1140
gccgccattt gtaatggtgg tggtggtgct cctctattg tcattgaaaa              1190

<210> SEQ ID NO 44
<211> LENGTH: 1383
<212> TYPE: DNA
<213> ORGANISM: Saccharomyces cerevisiae

<400> SEQUENCE: 44
```

```
ctatagtttg ctttcaatgt ttttgaccaa ttccttgtat ttctcagtag aataggactt      60
tggcctttca atggaagcac cgatggccct atcagtgatc aattgagcaa gaataccaaa     120
tgcccttgaa acgccaaata aaacggtata gaaagaagat tcttttagtc cataatattg     180
taataagaca ccagagtgag catctacatt tggccatgga ttttggttt taccatgttc      240
agtcaatacg ccaggtgcta cctcgtatat tgatgaaact aacttgaata attcataatc     300
tggaaaatgg tccatggcaa acttacgctg agccatataa cgaggatcag ttttccttag     360
cacagcatga ccataaccgg gaatgactct tcctgagttt agagtatccc ataaatattt     420
ttcgatcgta tctttagagt agtcatcatt tacctcttct ttaagtgcaa ataaccattc     480
tagtacttct tgattagcac gcccatgaag tgggccagcc aacccgttca aacctgatgc     540
aagggacaga taaggtgatg atagtgctga gcccacaaga tgggatgtat gtgcagatac     600
attaccacct tcgtgatccg aatgaatggt taaataaagt ctcatcaagt ccacgaaatc     660
ttcatcctta gaaccaatca agttgaccag attttttagca taatcggcat ttgggtccac    720
ttcacccatt ttgccatctt tgaatacatt acgataaatt ttagctgcaa taactggcaa    780
tttacccagc aagtctagtg aatcttcaaa agtataactc caataatctt gcttggaaat     840
tccttgagca taagccttag caaactttga ctcgctttcc aaggcagtta cagcaataga    900
gaattgagcc attgggtgta agtcctttgg taaattatcc aaaagttgaa cgacatgact    960
aggtagttcc gatcttgaca ttagatcagc tgataagttt tcaacttgcg cttgagttgg  1020
aacctcgcca gttagcaata accaaagag agcttctggt agtggttgtg agcttccttt    1080
tgccttgggc aggtcctttt gaatgtcggc gatcgtacga cctctgaaac gaataccgtc    1140
ttctgggtcc aaaacggaac cttcccatac gctccctgga atacctctca taccaccata    1200
tacctgttct aatagaacat cgctaatttt agttttgcca tgctctttaa cgaattgcct    1260
tacatcttga gcatggatgg ggtagatttc gctaaatctc tcttttagag tcttttcttg    1320
gcttgaattt gattgtaaat atgatgcaac atttctgttt gaatttagat aaggaactgt    1380
cat                                                               1383
```

```
<210> SEQ ID NO 45
<211> LENGTH: 1665
<212> TYPE: DNA
<213> ORGANISM: Saccharomyces cerevisiae

<400> SEQUENCE: 45
```

```
atggttaagg tcagtttgga taacgtcaaa ttactggtgg atgttgataa ggagcctttc      60
tttaaaccat ctagtactac agtgggagat attcttacca aggatgctct agagttcatt    120
gttcttttac acagaacttt caacaacaag agaaaacaat tattggaaaa cagacaagtt    180
gttcagaaga aattagactc gggctcctat catctggatt tcctgcctga aactgcaaat    240
attagaaatg atcccacttg gcaaggtcca attttggcac cggggttaat taataggtca    300
acggaaatca cagggcctcc attgagaaat atgctgatca acgctttgaa tgctcctgtg    360
aacacctata tgactgattt tgaagattca gcttcaccta cttggaacaa catggtttac    420
ggtcaagtta atctctacga cgcgatcaga atcaaatcg attttgacac accaagaaaa    480
tcgtacaaat tgaatggaaa tgtggccaac ttgcccacta ttatcgtgag accccgtggt    540
tggcacatgg tggaaaagca cctttatgta gatgatgaac caatcagcgc ttccatcttt    600
gattttggtt tatatttcta ccataatgcc aagaattaa tcaaattggg caaaggtcct    660
tacttctatt tgccaaagat ggagcaccac ttggaagcta aactatggaa cgacgtcttc    720
```

```
tgtgtagctc aagattacat tgggatccca aggggtacaa tcagagctac tgtgttgatt      780
gaaactttgc ctgctgcttt ccaaatggaa gagatcatct atcaattaag acaacattct      840
agtgggttga attgcggacg ttgggactat attttctcta caatcaagag attaagaaat      900
gatcctaatc acattttgcc caatagaaat caagtgacta tgacttcccc attcatggat      960
gcatacgtga aaagattaat caatacctgt catcggaggg gtgttcatgc catgggtggt     1020
atggctgcgc aaatccctat caaagacgac ccggcagcca tgaaaaggc catgactaaa      1080 gtccgtaatg ataagattag agagctgaca aatggacatg atgggtcatg ggttgcacac     1140
ccagcactgg cccctatttg taatgaagtt ttcattaata tgggaacacc aaaccaaatc     1200
tatttcattc ctgaaaacgt tgtaacggct gctaatctgc tggaaaccaa aattccaaat     1260
ggtgagatta ctaccgaggg aattgtacaa aacttggata tcgggttgca gtacatggaa     1320
gcttggctca gaggctctgg atgtgtgccc atcaacaact tgatggaaga cgccgccact     1380
gctgaagtgt ctcgttgtca attgtatcaa tgggtgaaac acgtgttac tctaaaggac      1440 acgggagaaa aggtcacccc agaattaacc gaaaagattc taaaagaaca agtggaaaga     1500
ctgtctaagg caagtccatt gggtgacaag aacaaattcg cgctggccgc taagtatttc     1560
ttgccagaaa tcagaggcga gaaattcagt gaattttga ctacattgtt gtacgacgaa      1620
attgtgtcca ctaaggcgac gcccactgat ttgagcaaat gtga                      1665

<210> SEQ ID NO 46
<211> LENGTH: 1665
<212> TYPE: DNA
<213> ORGANISM: Artificial
<220> FEATURE:
<223> OTHER INFORMATION: Synthetic sequence

<400> SEQUENCE: 46
atggaccaca tgtctaccca gcaggttagc tccgagaata tcgttcgcaa cgcggcgaac       60
ttccacccga atatctgggg taatcatttc ttgacgtgtc caagccagac gatcgattct      120
tggacgcaac aacaccataa agagctgaaa gaagaggtcc gcaagatgat ggtgagcgac      180
gcaaacaaac cggcacaacg tctgcgtctg attgacaccg ttcaacgttt gggcgtggcg      240
tatcatttcg aaaagaaat cgatgacgct ctggaaaaga tcggtcacga tccgtttgac       300
gataaggatg acctgtatat cgttagcctg tgttttcgcc tgctgcgtca gcatggcatc      360
aagattagct gcgatgtttt tgagaagttc aaagacgacg atggcaagtt taaggcttcc     420
ctgatgaatg atgtccaagg tatgctgtcg ttgtatgaag cggcccacct ggcaattcat      480
ggcgaggaca tcctggatga ggctattgtc tttacgacca cccacctgaa gagcaccgtt      540
tctaactccc cggtcaattc caccttgcg gaacagattc gccacagcct gcgtgtgccg       600
ctgcgtaagg cagtcccgcg tttggagagc cgctacttcc tggatatcta gccgtgac       660 gacctgcacg acaagactct gctgaacttt gccaaactgg acttcaacat cctgcaggcg     720
atgcaccaga agaggcaag cgagatgacc cgttggtggc gtgatttcga tttcctgaag      780
aagctgccgt acattcgtga tcgcgtggtt gaactgtact tttggatttt ggtcggtgtg     840
agctaccaac cgaaattcag cacgggtcgt atcttttga gcaagattat ctgtctggaa      900 acctggtgg acgacacgtt tgatgcgtac ggtactttcg acgaactggc cattttcacc      960
gaggccgtta cgcgttggga cctgggtcat cgcgacgcgc tgcctgagta catgaaattc     1020
attttcaaga ccctgattga tgtgtacagc gaggcggaac aagagctggc aaaagaggc     1080
```

| | |
|---|---|
| cgctcctata gcattcacta tgcgatccgt agcttccagg agttggtcat gaagtacttt | 1140 |
| tgcgaggcga atggctgaa taagggttat gttccgagcc tggatgacta caagagcgtc | 1200 |
| agcctgcgca gcatcggctt cctgccgatc gccgtggctt cttttgtttt catgggcgac | 1260 |
| attgctacga aagaggtttt tgagtgggaa atgaataacc cgaaaatcat catcgcagcc | 1320 |
| gaaaccattt tccgctttct ggatgacatt gcaggtcatc gcttcgaaca aaaacgtgag | 1380 |
| cacagcccga gcgcaatcga gtgctacaaa aaccaacatg gtgtctcgga agaagaggca | 1440 |
| gtgaaagcgc tgagcttgga ggtcgccaat tcgtggaaag acattaacga agagctgctg | 1500 |
| ctgaacccta tggcaattcc actgccgttg ctgcaggtga tcctggattt gagccgtagc | 1560 |
| gcggacttca tgtacggtaa tgcgcaggac cgtttcacgc actccaccat gatgaaagat | 1620 |
| caagttgacc tggttctgaa agatccggtg aaactggacg attaa | 1665 |

<210> SEQ ID NO 47
<211> LENGTH: 849
<212> TYPE: DNA
<213> ORGANISM: Artificial
<220> FEATURE:
<223> OTHER INFORMATION: Synthetic sequence

<400> SEQUENCE: 47

| | |
|---|---|
| atgaaaaaga tattcgttct gggcgctggt acaatgggtg caggtatcgt acaagccttc | 60 |
| gcacaaaaag gatgtgaagt tatcgtccgt gacataaagg aagagtttgt cgacagaggt | 120 |
| atcgcaggaa tcacaaaagg attggaaaaa caagtggcaa agggaaaat gtcagaggaa | 180 |
| gataaggagg caattctatc taggattagt ggtactactg acatgaaatt ggctgctgat | 240 |
| tgtgatctag ttgtcgaagc agcaatcgaa acatgaaaa tcaaaaagga gatctttgct | 300 |
| gaattagacg gtatttgcaa acctgaagct atacttgcct ctaatacatc atcactgagt | 360 |
| ataacagaag ttgcctccgc tactaaaaga cctgacaaag ttattggcat gcacttttc | 420 |
| aaccctgcac cagtaatgaa gttagttgaa atcatcaaag gcatcgcaac atctcaggaa | 480 |
| acctttgatg ctgttaagga attgtcagtg gcaattggaa aagagcctgt cgaagtagca | 540 |
| gaagccccag ggtttgttgt caatagaatc ttgattccta tgataaacga ggcttccttc | 600 |
| atcttacaag agggcatagc ctcagtagaa gatattgata ctgctatgaa atacggtgct | 660 |
| aatcatccaa tgggtccact ggctttaggc gacttgattg gattagatgt gtgtttagct | 720 |
| atcatggatg tcctattcac cgaaactgga gacaataagt atagagcctc ttccattttg | 780 |
| agaaagtacg tgagagccgg ttggcttggt agaaagtctg gtaaggggtt ttacgattac | 840 |
| tctaagtaa | 849 |

<210> SEQ ID NO 48
<211> LENGTH: 794
<212> TYPE: DNA
<213> ORGANISM: Artificial
<220> FEATURE:
<223> OTHER INFORMATION: Synthetic sequence

<400> SEQUENCE: 48

| | |
|---|---|
| atggagttga aaacgtgat cttagaaaag gaaggtcact tagctatagt taccatcaat | 60 |
| agacctaaag ccctaaacgc tttgaattca gaaactctga agatttgga tgccgtatta | 120 |
| gaagatcttg aaaagagtatt taacatgtac actgtaattg tcacaggtgc aggagaaaag | 180 |
| tccttcgtcg ctggagctga catctctgaa atgaaagatc tgaatgagga acaaggaaag | 240 |
| gagttcggca ttctggggaa taacgttttt cgtaggttag aaagattgga taagcctgtg | 300 |

```
atagcagcca tttcaggttt tgcacttggt ggcgggtgtg agttggcaat gagttgcgat    360
atcagaatag cctctgttaa agcaaagttc ggacaaccag aagccggttt aggtattaca    420
cctggctttg ggggcacaca aagactagct agaattgttg cccaggtaa agctaaagag     480 cttatctaca cttgcgactt gatcaatgct gaagaggcat acagaattgg tttggttaac    540
aaagtagtcg aattggaaaa gttaatggag gaagctaagg caatggctaa caaaatcgca    600
gccaatgctc caaaagccgt tgcctattgt aaagacgcca ttgacagagg aatgcaagtg    660
gacatcgatg cagctatcct tatcgaagca aagattttg gcaagtgttt tgctacagaa     720
gatcaaacag aaggtatgac tgcttttccta gagagaagag cagagaaaaa ctttcagaat    780
aagtaattaa ttaa                                                       794
```

```
<210> SEQ ID NO 49
<211> LENGTH: 1344
<212> TYPE: DNA
<213> ORGANISM: Artificial
<220> FEATURE:
<223> OTHER INFORMATION: Synthetic sequence

<400> SEQUENCE: 49
atgaccgtta aggacattct agacgccatt caatctaagg atgcaacttc cgcagacttt      60
gctgcactgc agcttccaga gtcatatagg gccattacag ttcataaaga tgaaactgaa     120
atgtttgctg gattagagac aagagataaa gatccaagga agtctattca tttggatgaa    180
gtgcctgtgc ctgaattggg acctggtgaa gctctagtag cagtaatggc ctctagtgtc    240
aattacaact ctgtgtggac ctcaatcttt gaacctgtat ctacattcgc cttttttggaa   300 agatatggga agttgtctcc attgacaaaa cgtcatgact taccatacca catcatcggg    360
tctgatctgg caggggtagt cctgagaacc ggtccaggtg taaacgcttg gcaacctggg    420
gatgaggttg tggctcactg cttaagtgta gaattagagt caccagatgg acatgatgac    480
actatgttag atcctgaaca gcgtatatgg ggcttcgaga ctaactttgg tggattggct    540
gaaatagcct tagtcaagac taatcaactt atgccaaagc caaaacatct tacctgggaa    600
gaggccgctg ctccaggttt ggtgaattcc acagcatacc gtcaattagt cagtagaaat    660
ggggcagcca tgaaacaagg cgacaatgtc ttgatatggg gtgcctcagg tggcttaggt    720
tcctatgcaa cacaatttgc tttggcaggt ggcgctaacc caatatgcgt tgtttcctct    780
cctcaaaaag cagagatttg taggtctatg ggagctgaag caatcattga tagaaatgct    840
gagggttaca aattctggaa agacgaacac actcaggacc caaaggaatg gaaaagattc    900
ggaaagagaa taagagaatt gactggtggt gaagatattg atatcgtttt cgaacaccca    960
ggtagagaga catttggagc ctcagtgtac gtcactagaa aaggtggcac aattaccacc   1020
tgtgcttcta catcaggata catgcatgaa tatgataaca gatatctttg gatgtccctt   1080
aagagaatca tcggcagtca ttttgccaat tacagaaag catacgaagc taacagacta    1140
attgcaaaag gcaaaatcca tcctactcta tcaaagactt actcactgga ggaaacaggt   1200
caagctgctt acgatgtaca cagaaaccta catcaaggta aggtgggcgt tttgtgtttg   1260
gctccagagg aaggactggg ggttagagat gctgaaatga gagcccagca catcgacgcc   1320
atcaacagat tcagaaatgt ttaa                                           1344
```

```
<210> SEQ ID NO 50
<211> LENGTH: 2595
<212> TYPE: DNA
```

<213> ORGANISM: Artificial
<220> FEATURE:
<223> OTHER INFORMATION: Synthetic sequence

<400> SEQUENCE: 50

| | | | | | |
|---|---|---|---|---|---|
| atgagagtta | ctaatcctga | agagctgact | aaaaggatcg | aacaaatcag | agaagcacaa | 60 |
| agggaattcg | ctaagttttc | tcaggaagag | gttgatgaaa | tctttagaca | agcagcaatg | 120 |
| gctgcaaatg | acgctcgtat | cactctagcc | aaaatggctg | tagaggaatc | aggtatgggt | 180 |
| attgtcgaag | ataaagtgat | caaaaaccat | tttgctgctg | aatacatcta | caatcaatac | 240 |
| aaagacacaa | aaacttgtgg | tgtaattgaa | agagatgaaa | tgtttggtat | cacacacata | 300 |
| gctgaaccaa | ttggcgtcat | agctgctatc | gttccaacta | caaaccctac | ttcaacagcc | 360 |
| atctttaaga | cattgatagc | tttgaaaacc | agaaatggga | taatcatttc | tccacatcct | 420 |
| agagccaaaa | actcaacaat | agccgcagct | aagattgttt | tagaagctgc | cgagagagct | 480 |
| ggagctccta | agggcatcat | tggttggatt | gatgaaccat | ccatcgaatt | gtctagaaac | 540 |
| gtcatggctg | aatcagatat | cattctggct | accggaggtc | caggtatggt | gagagcagca | 600 |
| tactcttcag | gtaaacctgc | aattggagtg | ggtgcaggaa | atacaccagc | catcattgat | 660 |
| gacacagcac | acattaagat | ggcagtgaat | tccatcttat | tgtctaaaac | atttgataat | 720 |
| ggcgtagtgt | gcgcatcaga | acaatccata | atcgctatgg | aatctgtata | tgacgaagtg | 780 |
| ttaaaggagc | tagacgaaag | aggagcctac | attttgagag | cgaggaaat | cgataaagta | 840 |
| aggtcaatca | tactggatag | taaaggttcc | cttaactcag | aaatagttgg | ccaatctgcc | 900 |
| tataagatag | caaagatggc | tggcgttgag | attagtgaag | ctgtcaaggt | acttattgga | 960 |
| gaagttgaat | cccctgaatt | ggaggagcct | ttttctcacg | aaaaactaag | tccaattcta | 1020 |
| gggatgtaca | agccaaaac | tttcgatgat | gctttgagac | tagcaagtag | aatgatcgaa | 1080 |
| ctaggggat | ttggtcacac | atccatcttg | tatactaatc | aaatggaatc | agtagataga | 1140 |
| atcgagaaat | tcgtgttgc | aatgaaaact | gccagaacct | tgattaacat | gcctgcttca | 1200 |
| caaggtgcta | ttggtgatat | ctacaacttt | aagttagcac | cttctctgac | cttgggatgt | 1260 |
| gggtcttggg | gtggcaattc | tatctctgaa | aatgttggcc | caaaacattt | gataaacgta | 1320 |
| aagagaattg | cagagagaag | agagaacatg | ttatggttcc | gtgttccaga | taagatatac | 1380 |
| ttcaaattcg | ggtgcttacc | agtcgcccta | gaagagttaa | acgccatgaa | aaagaagagg | 1440 |
| gcctttatcg | tcactgacag | agttctgttt | gatttggggt | atacacataa | gattacaaac | 1500 |
| atcctttctg | aaaaccacat | tgagtacaag | atattctccg | atgttgaacc | agatccaaca | 1560 |
| cttaaggctg | ccaagttagg | tgctgatgcc | atgagagact | tcaatcctga | cgtcatcatt | 1620 |
| gccattggtg | gaggcagtcc | aatggatgca | gccaaaatca | tgtgggtgat | gtacgaacat | 1680 |
| ccagacgtga | gatttgaaga | tctagccatg | aggtttatgg | acatcagaaa | aagagtctat | 1740 |
| gagttccctc | caatgggaga | aaaagcaatc | ttagtcgcca | ttcctacctc | tgccggaaca | 1800 |
| ggctcagaag | tcacaccatt | tgctgtaatc | accgaccaac | agacaggtgt | aaagtaccca | 1860 |
| ttagctgatt | atgctttgac | tcctaacatg | gcaatcatag | acgcagaact | tatgatgtct | 1920 |
| atgccaaaag | gttgactgc | tgcctctgga | attgacgctc | tggttcatgc | cattgaggct | 1980 |
| tacgtttctg | ttttggcatc | agaatacact | aatggtttgg | ccttagaagc | catacgtctt | 2040 |
| actttcaaat | accttcctga | tgcatacaat | ggtggcgcta | ccaatatcaa | ggcaagagag | 2100 |
| aaaatggctc | atgcatctag | tgttgcagga | atggcctttg | ctaatgcatt | tctaggcata | 2160 |
| tgtcactcta | tggctcacaa | gttgggtgct | ttccatcatg | ttccacatgg | cattgcaaac | 2220 |

```
gcccttctga tcgatgaagt gataagattc aatgctactg atgccccacg taagcaagca    2280
gcttttccac aatacaaata cccaaatgca ggctggaggt acgctagaat tgctgactac    2340
ttgaatcttg gaggtaatac agaggaagag aaggtagaat tactgattaa ggcaatcgat    2400
gacttaaagg ctaaggttgg aataccaaaa tccatcaaag agtttggggt ttcagaagag    2460
aaattctatg cctccatgga cgaaatggtg aacaagcat tcgacgatca gtgtacaggg    2520
gctaatccaa gatatccact aatgtctgaa atcaaagaca tgtacatcaa aagttacaat    2580
ggctcaaaca agtaa                                                    2595
```

<210> SEQ ID NO 51
<211> LENGTH: 1200
<212> TYPE: DNA
<213> ORGANISM: Artificial
<220> FEATURE:
<223> OTHER INFORMATION: Synthetic sequence

<400> SEQUENCE: 51

```
atgatagtaa agccaatggt aaggaacaat atctgtctta acgcccatcc acagggttgc     60
aaaaagggag ttgaagatca aattgaatac accaaaaaga gaattacagc agaggtcaag    120 gcagggcaa aggctcctaa gaacgtctta gttttgggtt gttctaatgg atacggcttg    180
gcaagtagaa taactgcagc cttcggttat ggagccgcca ctataggtgt atcattcgaa    240
aaagccggct ccgaaaccaa gtacggtaca cctggctggt ataacaatct gcttttgat    300 gaagctgcta agagaagg gttatactct gtcacaatag acggtgacgc atttctgat    360 gaaatcaaag ctcaggttat tgaagaggcc aagaaaaagg gtatcaaatt cgatctgata    420
gtatactcat tagcatcccc agtgcgtaca gatccagata ctggcattat gcacaaatct    480
gttttgaaac catttggaaa aactttcact ggtaaaacag ttgatccttt tacaggagaa    540
ctgaaggaaa tctcagctga accagctaat gatgaggagg cagctgctac tgtgaaagtt    600
atgggtggag aggactggga aagatggatc aaacaactaa gtaaggaagg tttacttgaa    660
gagggatgca tcaccttagc ctactcttac attggtcctg aagcaacaca agccctatac    720
cgtaaaggaa ctataggtaa ggcaaaggaa caccttgaag ctactgctca tcgtctgaat    780
aaggaaaatc catccattag ggctttcgtt agtgtcaaca aagggttagt taccagagca    840
tcagctgtga tccctgtcat tccactttac cttgcttcat tgtttaaggt tatgaaagag    900
aaaggcaatc atgaaggatg tatcgaacaa atcacaagat tgtacgctga gagattgtat    960
agaaaggatg gtacaattcc tgtggacgaa gagaatagaa ttagaatcga tgattgggag   1020
ttagaagagg acgttcaaaa agctgttttct gcattgatgg aaaaagttac aggcgaaaat   1080
gctgagtcac taacagacct ggcaggttat agacatgact ttttggcctc aaacgggttt   1140
gatgtagaag gtatcaacta cgaagctgaa gtcgaaagat tcgatagaat ctaagctagc   1200
```

<210> SEQ ID NO 52
<211> LENGTH: 1931
<212> TYPE: DNA
<213> ORGANISM: Artificial
<220> FEATURE:
<223> OTHER INFORMATION: Synthetic sequence

<400> SEQUENCE: 52

```
gcggccgcaa acaatgtca caaacacaca aacatgctat tcctgcgaat atcgctgaca     60
ggtgcttaat caaccctgaa caatacgaaa cgaagtacaa gcagtctatc aacgatcctg    120
```

-continued

| | |
|---|---|
| atactttctg gggcgagcaa ggtaagatac tcgattggat tactccatat caaaaggtca | 180 |
| aaaacacatc ctttgctcct ggaaatgtgt caatcaagtg gtacgaggac ggcactctaa | 240 |
| acctagctgc taattgcttg gatcgacacc tccaggaaaa tggtgacaga acggcaatca | 300 |
| tttgggaagg tgatgatact tctcaatcta agcacatctc ctacagagag ttacacagag | 360 |
| atgtttgcag attcgcgaat actttactgg acctgggtat caaaaagggc gatgttgtgg | 420 |
| caatctacat gcctatggtc ccagaggcag ctgtggcaat gttggcctgt gccagaatag | 480 |
| gagcagtcca tagcgttatc tttggcggat ctcccctga agccgttgct gggagaatca | 540 |
| ttgactcatc aagtagatta gttatcactg ccgacgaagg tgttagagca ggtagatcca | 600 |
| tcccattgaa gaaaaacgtt gatgacgcgt tgaaaaaccc aaacgttacg agtgtggagc | 660 |
| atgtaattgt actaaagcgt accggctctg atatagactg gcaggaaggt agggatttgt | 720 |
| ggtggagaga tcttattgag aaagcaagtc cagaacacca accagaagca atgaatgcgg | 780 |
| aagatccatt gttcatcttg tatacatctg ggtcaactgg caaaccaaaa ggtgttttgc | 840 |
| atacaacagg tggttatctc gtatacgccg caacaacctt taagtacgtt tttgattacc | 900 |
| atccaggtga tatctactgg gtgtaccgctg atgtcggttg ggttactggt catagttacc | 960 |
| tgctttacgg tccactggca tgcggcgcaa ccactttgat gtttgaagga gtaccaaact | 1020 |
| ggccaacccc agccaggatg tgtcaagtgg tcgataaaca ccaagtgaac atattgtaca | 1080 |
| cagccccaac cgccattaga gcgctaatgg ccgaaggaga taaggcgatt gagggaacag | 1140 |
| atagaagtag cctacgtatc ttaggatccg ttggcgagcc aatcaatcca gaagcttggg | 1200 |
| aatggtattg gaaaaagatt ggtaaggaaa agtgtccagt agtggataca tggtggcaaa | 1260 |
| ctgaaacagg tggattcatg attacacctc ttccaggtgc aatagaattg aaggctgggt | 1320 |
| ctgctactag gcctttcttc ggcgtccaac ctgctttagt agacaacgaa gggcatccac | 1380 |
| aagaggggc aacagaaggc aatctagtga taactgattc ctggcctggt caggctagaa | 1440 |
| cattgtttgg tgatcacgaa agattcgaac aaacctattt ctcaactttc aaaaacatgt | 1500 |
| atttcagcgg tgacggtgcg agaagagacg aagatgggta ctactggatt accggcagag | 1560 |
| tagatgacgt ccttaacgta tctggacatc gtctgggtac agctgagatt gagtcagctt | 1620 |
| tagttgctca tcctaagatt gctgaagctg cagtcgttgg catcccacac gctatcaagg | 1680 |
| gtcaagccat atacgcatat gttacactca accatggtga ggaaccatct ccagagctat | 1740 |
| acgcagaggt cagaaattgg gttcgaaagg aaatagggcc tttagccaca ccagatgttt | 1800 |
| tgcattggac agattcattg cctaagacaa gatctgaaaa gattatgaga cgtatactta | 1860 |
| gaaagatcgc cgccggagat acgtctaact taggtgatac ttctactctt gccgatccag | 1920 |
| gcgtggtcga a | 1931 |

<210> SEQ ID NO 53
<211> LENGTH: 1143
<212> TYPE: DNA
<213> ORGANISM: Artificial
<220> FEATURE:
<223> OTHER INFORMATION: Synthetic sequence

<400> SEQUENCE: 53

| | |
|---|---|
| atgaccgatg tggttattgt atctgcagct aggacagcag ttggtaagtt tggtggttct | 60 |
| ttagccaaaa ttccagctcc cgaattgggg gctgtcgtta taaaggcagc tttagaaagg | 120 |
| gcaggagtaa aaccagaaca agtgagcgaa gtaattatgg gtcaagtcct aacagcgggt | 180 |
| tcaggccaga accctgcgag gcaagcagca attaaggcag gactacctgc gatggtgcct | 240 |

```
gcaatgacga ttaataaggt gtgtggttca ggtttgaagg ccgtaatgtt agccgcaaat    300
gctatcatgg ccggtgatgc cgagattgtg gttgccggag gccaagaaaa catgtctgct    360
gctcctcatg tcctgccggg ttctagggat gggtttagaa tgggtgacgc taaacttgtg    420
gatactatga tagtagatgg tctttgggat gtatacaatc agtaccatat gggtattacg    480
gccgagaacg tggctaaaga atatggaatt cgagagaag ctcaagatga attcgccgta    540
ggttcccaaa ataaggcaga agctgctcaa aaggctggga aatttgacga agaaattgtt    600
ccagtgttaa taccacagag gaaaggtgat ccagtggctt tcaaaacaga tgagtttgtt    660
agacaaggtg ctactttaga ttcaatgagc ggattaaagc ctgcatttga taaggcgggc    720
accgttacag cagcaaacgc ttcaggtcta aatgatggag cagctgctgt cgttgtcatg    780
agtgcagcca aggctaagga attgggttta acccctcttg caactattaa atcatatgcc    840
aacgccggtg ttgacccaaa agttatgggt atgggtcctg tgccagcttc gaaaagggct    900
ttgtccagag cggagtggac tccccaggat ttggacttga tggaaatcaa tgaagctttt    960
gcagcacagg ctctagcggt gcaccagcaa atgggttggg atacctctaa ggtaaacgtt   1020
aacggtggag cgattgctat aggccatcct ataggtgctt cgggatgtag gattttggta   1080
acattgttgc atgaaatgaa acgtagagat gccaaaaagg gtttagcttc tttatgtatt   1140
ggg                                                                 1143

<210> SEQ ID NO 54
<211> LENGTH: 620
<212> TYPE: DNA
<213> ORGANISM: Artificial
<220> FEATURE:
<223> OTHER INFORMATION: Synthetic sequence

<400> SEQUENCE: 54
atgacacaaa gaattgcata tgtaactggc ggaatgggtg gaatcggtac agcaatttgc     60
cagcgtttag caaaggatgg tttcagagtg gttgctggtt gcggtccaaa tagtcctcgt    120
agagagaagt ggctggagca acaaaaagcc ttagggtttg actttattgc cagcgaaggt    180
aatgtagcag attgggactc taccaaaacg gcttttgaca aagttaagtc agaagtcggg    240
gaagtagatg ttttgattaa caatgcgggt ataactcgtg atgtcgtgtt taggaagatg    300
actagagcag actgggatgc tgttatagat acaaatctta catcgctatt taatgttaca    360
aagcaagtga ttgatggcat ggccgatagg ggctggggaa gaatcgtaaa catcagttcg    420
gtcaatggtc agaaaggtca gttcggacag accaattatt ctacggctaa ggctgggttg    480
catggcttca ctatggcatt ggctcaagaa gttgcaacga aaggtgtaac tgtaaataca    540
gtctccccag gatatattgc aaccgatatg gtgaaggcaa ttaggcaaga cgttctagac    600
aagattgtcg ccactatacc                                                620

<210> SEQ ID NO 55
<211> LENGTH: 1770
<212> TYPE: DNA
<213> ORGANISM: Artificial
<220> FEATURE:
<223> OTHER INFORMATION: Synthetic sequence

<400> SEQUENCE: 55
atggcaactg gtaaaggtgc tgctgcatct actcaagaag gaaaatcaca acccttaag      60 gttacacctg gcccttttga tccagctacc tggctggaat ggtccaggca atggcagggt    120
```

```
-continued acagagggta atggccatgc agctgcctcc ggtattccag gtttagatgc cttagcaggt     180
gttaaaatag ctccagctca gcttggcgat atccaacaga gatatatgaa agatttttcc     240
gcactttggc aggccatggc tgaagggaag gctgaagcta caggtccact gcatgatagg     300
agatttgctg gagacgcatg gaggaccaat ttgccataca gattcgcagc ggccttctat     360
ttactgaatg caagagccct tacagagcta gccgatgcag tcgaagcgga tgctaaaacg     420
cgtcagagaa tcaggttcgc aatatctcaa tgggtagatg caatgagtcc tgcaaatttc     480
ttggctacaa atcctgaagc acaaagactg ttaattgaat caggtggcga gagtttacgt     540
gcaggtgtga gaaatatgat ggaggattta acaaggggaa aaatatccca aactgatgaa     600
tcagcttttg aagtgggtag aaacgttgcg gttaccgagg gagctgtcgt ttttgaaaat     660
gaatattttc aacttttgca atacaaacca ttgacagata aagtacacgc taggcctctg     720
ttgatggttc ctccttgtat caacaagtat tacatccttg atttgcagcc tgaatcctca     780
cttgttagac atgtagtaga acaaggtcac acagtatttt tggttagttg gagaaatccc     840
gatgcttcga tggcgggttc aacatgggat gattatatag aacatgccgc aataagagct     900
atcgaagttg ctagggatat ctctggtcaa gataaaatca atgtattagg gttttgcgtc     960
gggggtacta tcgtttcaac cgcgttggca gttcttgctg caaggggaga acatcctgca    1020
gcaagcgtaa cactattaac cacactacta gattttgctg atactggaat acttgatgtg    1080
tttgttgacg agggtcatgt tcaactacgt gaggcgactt tgggaggtgg cgcaggagcg    1140
ccttgtgccc tacttcgtgg tttagaatta gcaaacacat tcagctttt aaggcctaac     1200 gacctagttt ggaactacgt cgttgataac tacttgaaag gcaatactcc tgttcctttc    1260
gacttgttgt tctggaacgg tgatgctacc aacttgccag gtccctggta ctgttggtat    1320
ctaagacata catacttgca aaatgagtta aaggttcccg gtaaattgac agtgtgtgga    1380
gttccagtcg attttagcaag tatagacgtt cccacttaca tttacggaag cagagaagat    1440
cacattgttc cttggactgc agcatacgct tctaccgcac ttttggccaa caagttaagg    1500
ttcgttttgg gagcctctgg acatatagca ggagtaatca atcctcctgc taaaaacaaa    1560
cgttctcatt ggacaaatga tgctttacca gagtcaccac aacaatggtt ggccggtgcg    1620
atagaacatc atggctcttg gtggcctgac tggacagcct ggctagctgg acaagccgga    1680
gcaaaacgtg ctgcacccgc caattacggg aatgcaagat atagggcaat agagccggca    1740
cccggtaggt atgttaaggc aaaagcatag                                      1770
```